(12) United States Patent
Van Heugten

(10) Patent No.: US 7,594,729 B2
(45) Date of Patent: Sep. 29, 2009

(54) WAVEFRONT SENSOR

(75) Inventor: Anthony Y. Van Heugten, Sarasota, FL (US)

(73) Assignee: WF Systems, LLC, Roanoke, VA (US)

( * ) Notice: Subject to any disclaimer, the term of this patent is extended or adjusted under 35 U.S.C. 154(b) by 0 days.

(21) Appl. No.: 11/945,028

(22) Filed: Nov. 26, 2007

(65) Prior Publication Data
US 2009/0109401 A1    Apr. 30, 2009

Related U.S. Application Data

(60) Provisional application No. 61/001,042, filed on Oct. 31, 2007.

(51) Int. Cl.
*A61B 3/10* (2006.01)
(52) U.S. Cl. .................... 351/221; 351/205
(58) Field of Classification Search .......... 351/221, 351/205, 206, 209, 210, 211, 212, 213, 216, 351/246; 356/123, 125; 359/641
See application file for complete search history.

(56) References Cited

U.S. PATENT DOCUMENTS

| 5,963,300 | A | 10/1999 | Horwitz |
| 6,270,221 | B1 | 8/2001 | Liang et al. |
| 6,561,648 | B2 * | 5/2003 | Thomas .................. 351/221 |
| 6,736,510 | B1 | 5/2004 | Van Heugten |
| 6,819,413 | B2 | 11/2004 | Neal et al. |

FOREIGN PATENT DOCUMENTS

WO    WO 92/01417    2/1992

OTHER PUBLICATIONS

The International Search Report and Written Opinion, mailed Jan. 5, 2009, issued in related International Patent Application No. PCT/US08/81584, filed Oct. 29, 2008.
T. Van Heugten et al., "Validation of Novel Hartmann-Moire Wavefront Sensor with Large Dynamic Range", presented at Wavefront Congress, Feb. 17, 2008, available at http://www.wavefront-congress.org/info/listing_details.asp?absID-12, last visited Feb. 25, 2008.

* cited by examiner

*Primary Examiner*—Hung X Dang
(74) *Attorney, Agent, or Firm*—Townsend and Townsend and Crew, LLP

(57) ABSTRACT

The present invention relates to a wavefront sensor using a pair of screens, each having a two-dimensional array of circular apertures, to achieve Moiré effects, and its use to measure the slope of a wavefront.

36 Claims, 36 Drawing Sheets

0 degrees of rotation

WAVEFRONT SENSOR

CROSS-REFERENCES TO RELATED APPLICATIONS

This application claims the benefit of U.S. Provisional Patent Application No. 61/001,042 filed Oct. 31, 2007, which is incorporated herein by reference.

BACKGROUND OF THE INVENTION

A wavefront sensor is a device for measuring the aberrations of an optical wavefront. Hartmann developed the Hartmann Test over one hundred years ago, yet the Hartmann class of wavefront sensors continues to be the most commonly used type of wavefront sensors to this time.

The first Hartmann Test was simply a screen, a sheet of material with a series of holes cut into it. The Hartmann screen was placed at the opening of a telescope and then viewed with the telescope's optics, either lenses or mirrors. If there was any deviation in the location of the holes of the Hartmann screen observed in the image of the Hartmann screen created by the telescope optics, then a defect was present in the telescope optics. In other words, aberrations were present in the telescope optics.

Shack modified the Hartmann test by adding a lens (also called a lenslet) into each of the holes in the Hartmann screen. The Hartmann screen with lenslets is known as the Shack-Hartmann system. Each lenslet has a controllable focal length, allowing a longer focal length than a hole without a lens could create to be introduced into the system. A hole with no lens will act as a pin-hole camera and cause a spot of light to be formed some distance downstream in the direction of the flow of light.

Liang et al. modified the Shack-Hartmann system by adapting its use to measuring the wavefront of the human eye. See U.S. Pat. No. 6,270,221.

The theory of operation when using a simple Hartmann screen as a wavefront sensor is to pass light through the Hartmann screen, then observe the location shift of the spots formed by the holes. The shift in location of the spot is a direct indicator of the angle of the light that passed through the hole, relative to the perpendicular axis. For example, if light approached and then passed through the Hartmann screen perpendicular to the flat surface of the screen (a flat wavefront), the light would form a spot at a small distance downstream to the flow of light, and the spot would appear to be in the center of the hole when viewed from the downstream side of the Hartmann screen if the observer was looking at the Hartmann screen perpendicularly. However, if the light approached the Hartmann screen at an angle, for example, if the light approached the screen such that the light's source was below the perpendicular axis of the Hartmann screen and rising up, then the points of light formed by the holes would be above the apparent center of the holes of the Hartmann screen. With the use of basic trigonometry, the distance of the lateral shift of the point of light, coupled with the distance that the point of light is away from the hole, can be used to calculate the angle of the approach of light. The spots of light form at various distances downstream from the holes, and this must be either measured or calculated in the conditions at which the light will be analyzed. These distances are known to those skilled in the art of optics.

In the case of measuring light in a manner useful to optical applications, the complex shape of the light wave must be measured. In these cases, each point of light is individually measured for movement, and the angle of light, or in other words, its slope, can be measured at each of the numerous individual locations, allowing a complex analysis to occur.

The angle (or slope) of the approaching light to be analyzed is usually very small in most optical applications. For example, with human eyes, refraction is measured in diopters. If, for example, an eye had one diopter of refractive error, the angle of the light to be measured from a six mm pupil is only one third of a degree. If light from this eye were passed through a Hartmann screen and formed a spot of light at a distance of 4 mm downstream, the spot will have shifted off-center by only 0.023 mm. Such a small shift can be difficult to detect and measure.

When lenses are added to the Hartmann screen (a Shack-Hartmann wavefront sensor), the distance between the spot of light and the screen can be increased, thereby increasing the lateral movement of the spots for any given angle of light approaching the device. This axial distance could be controlled by the focal distance of the lens. For example, if the same one diopter light beam described in the preceding paragraph were used with typical Shack-Hartmann lenslet array with lenses having a 20 mm focal distance, the spot would shift 0.115 mm laterally (vs. 0.023 mm along a 4 mm axial distance). This increased lateral movement of 500% results in a 500% improvement to the sensitivity of the system.

However, this increase in sensitivity comes at the price of reducing the range of measurement of the device. By extending the distance that the spots of light formed away from the Hartmann screen, the Shack-Hartmann wavefront sensor causes a simultaneous increase in the variability of the shift in the axial distance that occurs along with the shift in the lateral distance, causing the spots to become no longer in the focus plane of the observing camera, which is used to detect the spot movement. With both systems, the Hartmann Screen and the Shack-Hartmann, as the spots of light shift laterally, they also shift axially, or lengthwise. For example, with a diverging wavefront passing through the system, the spots of light will all appear to be moving radially outward from each other, but they will also be moving further downstream from the holes and/or the lenses. In the case of the Hartmann Screen, the movement in both directions, laterally and axially, is less than the amount of movement caused by the Shack-Hartmann device. The axial movement of the Hartmann Screen spots is considerably less than the axial movement of the Shack-Hartmann spots, and consequently, the spots remain in focus of the observing camera throughout a higher range of measurement than the Shack-Hartmann device.

Hence, the Hartmann Screen has higher dynamic range of measurement but lower sensitivity to small light shifts, while the Shack-Hartmann system has lower dynamic range of measurement but higher sensitivity to small light shifts. Increased sensitivity comes at the expense of range, and increased range comes at the expense of sensitivity in these devices.

Many efforts have been made to overcome this deficiency in the Shack-Hartmann system. A review of the literature in the public domain will yield many examples of such efforts, but all of these efforts require that the system be made more complex with such things as moving optical parts, higher resolution, more expensive cameras, complex sub-pixel analysis, etc.

A different optical system is the Talbot wavefront sensing method (also a concept known for more than one hundred years). Talbot optics are optics made from rulings (a series of parallel lines cut into or etched onto a clear object), or cross gratings, which are two sets of parallel rulings intersecting each other at a cross angle, which cause a self-imaging pattern of lines or cross lines to form in space a predicted distance away from the Talbot optic called "shadow patterns," with the distance based upon factors such as the wavelength of light and the spacing of the ruling lines. The location of these shadow lines would move based upon the angle of light passing through the Talbot optic, but they too would move only small amounts.

To increase the movement of the shadow patterns, the Moiré effect was employed with the Talbot (or other shadow-creating) optics. U.S. Pat. No. 5,963,300 to Horwitz and U.S. Pat. No. 6,736,510 to Van Heugten describe Talbot wavefront sensing systems with the use of Moiré effects. Horwitz placed a second, identical Talbot optic behind the first Talbot optic, then rotated the second Talbot optic slightly with respect to the first Talbot optic. By doing so, the shadow pattern's movement was amplified, making the movement easier to detect. Both devices described in these patents used rulings or gratings to produce shadows and did not use Hartmann optics with circular apertures to produce light spots of concentrated, focused beams.

A moving shadow pattern (as in Talbot or Talbot Moiré) differs from the moving spots (as in the Hartmann Screen or the Shack-Hartmann device). Hartmann screens do not merely form shadows or shadow patterns, they form focused spots of light due to the holes acting as pinhole cameras, concentrating a beam diameter down to a smaller beam diameter, or a point. Shack-Hartmann devices also do not form shadow patterns; they form focused spots of light due to the lenslets refracting the light, also concentrating a beam diameter down to a smaller beam, or a point. The moving shadow patterns are not as localized and can not be measured for centration as well as the moving spots of Hartmann devices. Other advantages of moving spots versus shadows include that Hartmann-based optics can form spot patterns of light at a narrower plane from polychromatic light, whereas Talbot optics create a thicker plane which cannot be imaged by a camera as easily, if at all. This allows Hartmann-based optics to examine beams of light in multiple wavelengths if necessary, which is particularly useful when measuring the human eye, whereas Talbot based optics are limited to function in narrower wavelength bands of light. Another advantage is that in today's wavefront sensor, CCD cameras are used to view the images. CCD cameras have square pixels aligned in rows and columns, causing aliasing distortions when the shadow lines formed by Talbot optics that utilize rulings or gratings align with the rows of pixels, which interferes with the analysis. Hartmann-based optics create circular spots, which do not create this aliasing problem. Another advantage of Hartmann-based optics is that because the spots formed are circular, more efficient centroiding algorithms may be used, which cannot be used as efficiently upon the lines or squares formed by Talbot optics.

There is a need for wavefront sensors that can achieve both high sensitivity and a high dynamic range of measurement. There is also a need for wavefront sensors that result in a high image quality. There is also a need for wavefront sensors that are small, lightweight, inexpensive, versatile, and simple.

BRIEF SUMMARY OF THE INVENTION

The present invention is directed to an apparatus comprising two screens, each having a two-dimensional array of circular apertures, wherein the second screen is rotated with respect to the first screen, thereby creating a Moiré effect.

BRIEF DESCRIPTION OF THE DRAWINGS

FIG. 36A shows an emmetropic eye.

FIG. 37A shows an emmetropic eye.

FIG. 38A shows an emmetropic eye.

DETAILED DESCRIPTION OF THE INVENTION

The novel wavefront sensor described herein utilizes two screens that are rotated relative to each other to create Moiré effects to amplify the movement of the spots created by a light beam passing through a Hartmann screen. By rotating the two screens, the axial (lengthwise) distance that the spots form downstream from the screen may be reduced by design, allowing greater dynamic range of measurement. Simultaneously, the lateral movement is increased, allowing greater sensitivity to measure smaller wavefront slopes.

In one embodiment, the apparatus of the present invention comprises: a first screen comprising a first two-dimensional array of circular apertures, wherein the first screen is placed downstream of a light source; a second screen comprising a second two-dimensional array of circular apertures, wherein the second screen is placed downstream of the first screen, the second screen is in a plane parallel to the first screen, and the second screen is rotated relative to the first screen; and a light detector downstream of the second screen.

Figure 1:
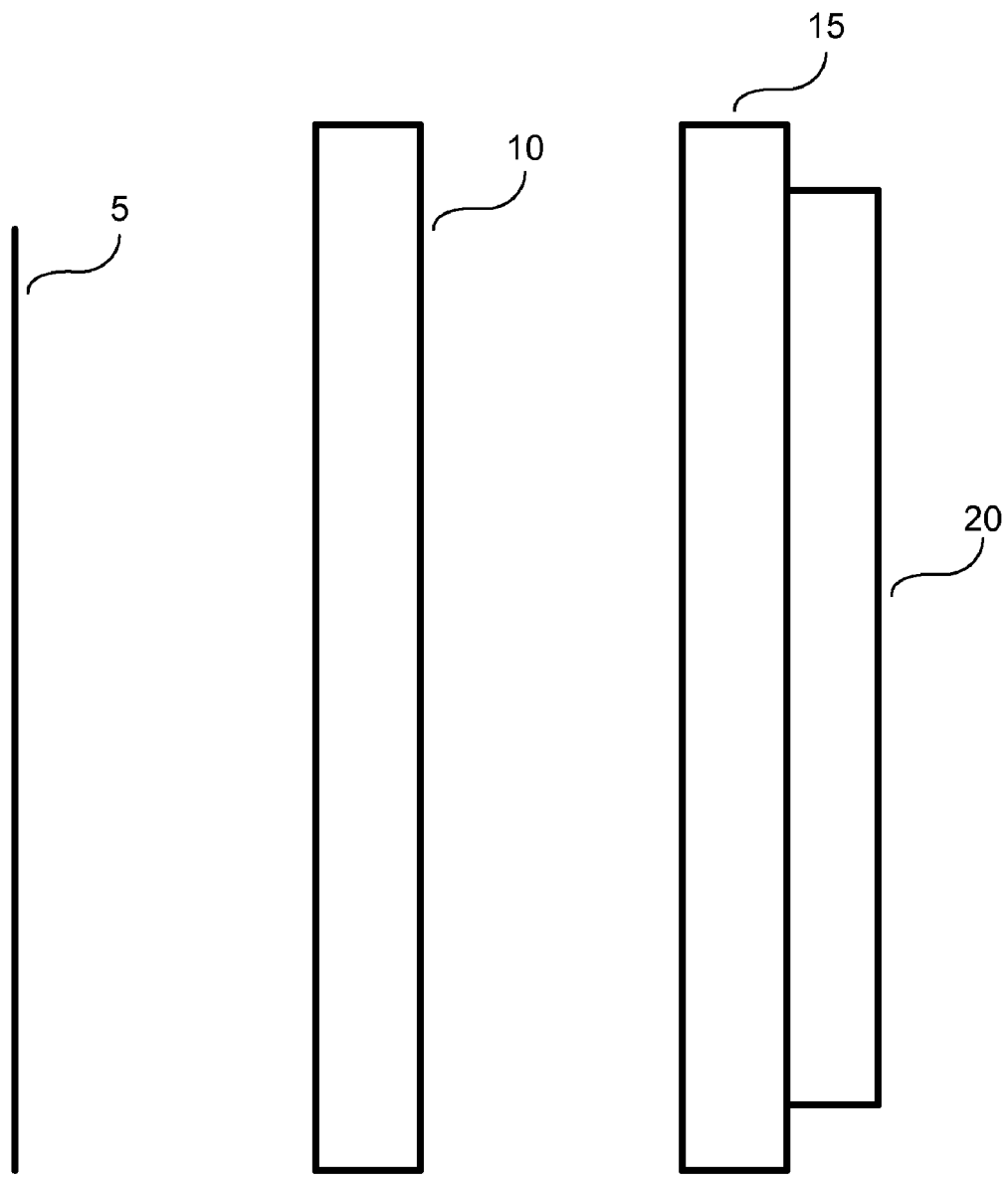
FIG. 1 shows an exemplary optical layout of the components from a side perspective.

As shown in FIG. 1, the first screen (10) is placed downstream of a light beam to be analyzed, a second screen (15) is placed downstream of the first screen, and a light detector (20) is placed downstream of the second screen. "Downstream" means further from the light beam's source on the path traveled by the light beam. In one embodiment, the light source will project a plane light wave (5) that propagates from left to right, becomes incident upon a first Hartmann screen (10), passes through the first Hartmann screen (10), becomes incident upon a second Hartmann screen (15), passes through the second Hartman screen (15), and then becomes incident upon the light detector (20). In one embodiment, the holes of the second screen (15) are on the right side of the optic in the drawing orientation of FIG. 1.

In one embodiment, the light detector (20) can convert light to electronic signals, which can be fed into a computer for analysis. Methods of feeding such data into a computer are known to those skilled in the art of Machine Vision. For example, a charge-coupled device (CCD) light detector, such as a Watec LCL 903 K CCD camera, Point Grey FL2 CCD camera, or other commercially available CCD camera, can be connected to an IMperx Frame Grabber, or other commercially available frame grabber, that allows the light images to be placed into computer memory for analysis.

Figure 2:
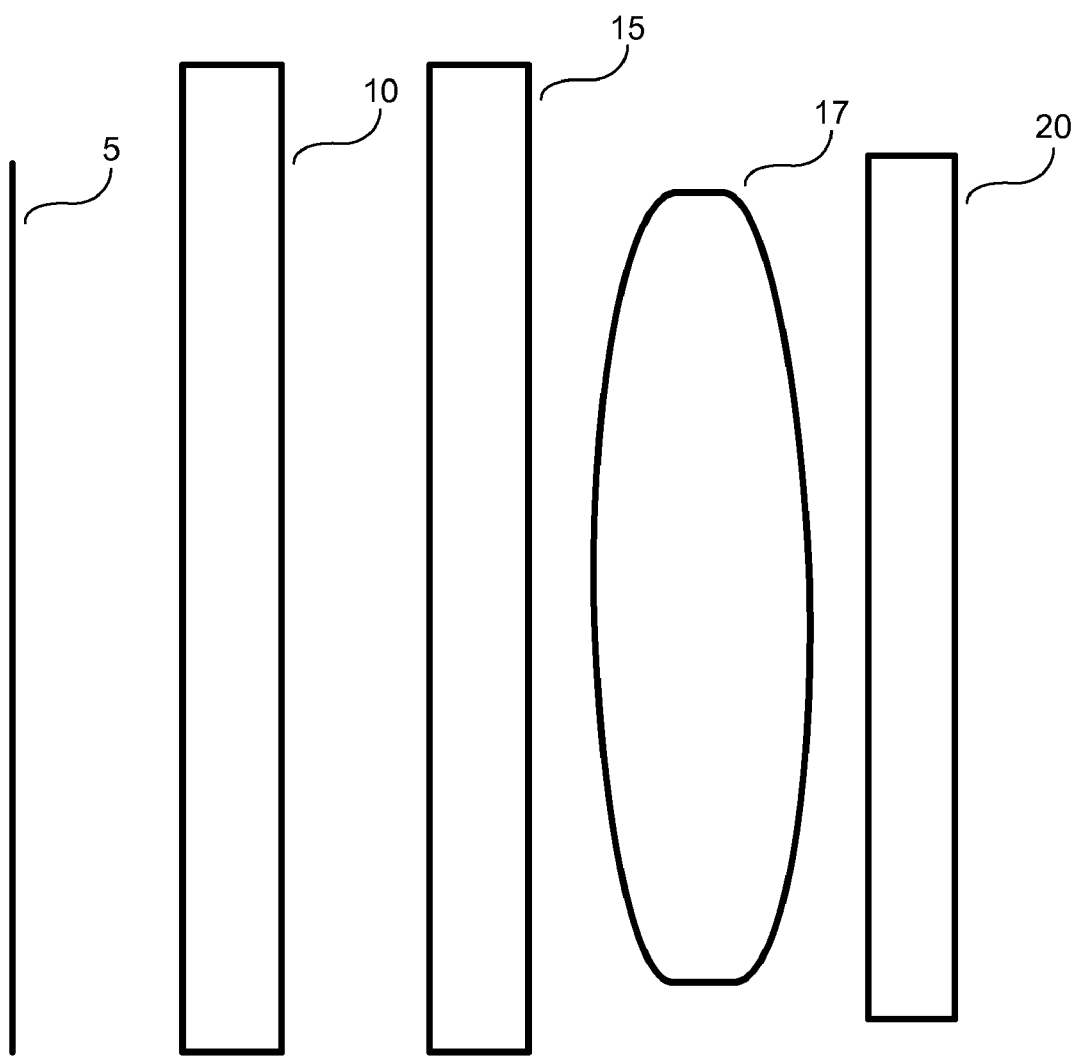
FIG. 2 shows an alternative optical layout, also from a side perspective.

FIG. 2 shows an alternative embodiment for allowing light detector (20) to accept and convert the light to electronic signals. A relay lens (17) is placed between the second screen (15) and the light detector (20), allowing the spot patterns formed by the second screen (15) to come into focus upon the light detector (20). Another position for a relay lens can be upstream of the first screen, e.g., between the light source (5) and the first screen (10). One or more lenses can be placed in one or both of these positions. Such relay optics and their design are known to those skilled in the art of optics design. An exemplary lens (17) is an Edmund Optics Triplet with a focal distance of 25 mm.

Each screen comprises a two-dimensional array of circular apertures. The two-dimensional array of circular apertures can include, for example, an array of rows and columns, but the circular apertures may be arranged in other orthogonal or non-orthogonal two-dimensional arrays. The first and second screens can have an array that is the same as, or in some cases, different from one another.

Figure 3:
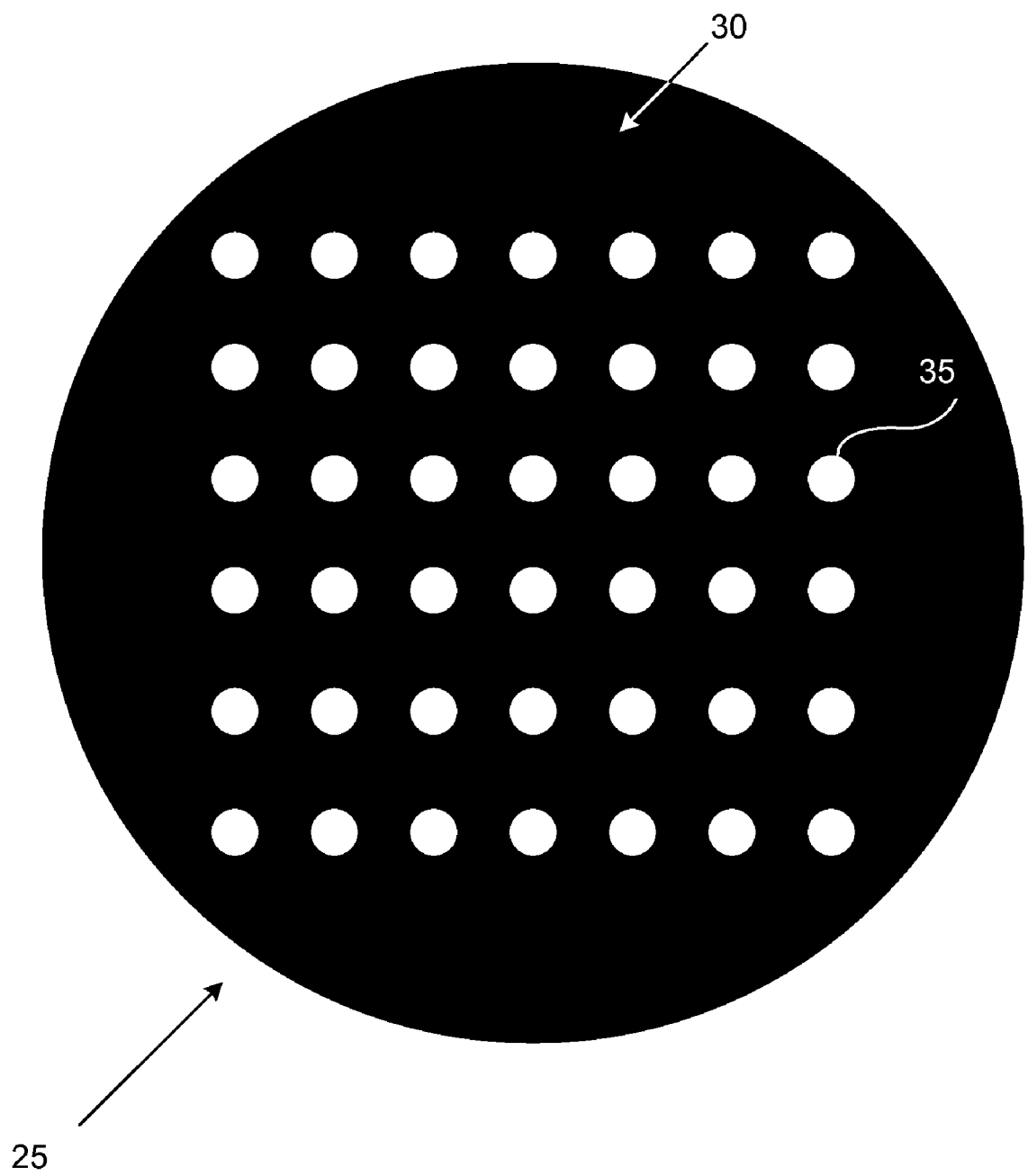
FIG. 3 shows the layout of a Hartmann screen.

Either one or both of the screens can be Hartmann screens. In one embodiment, both of the screens are Hartmann screens. FIG. 3 shows an example layout of a Hartmann screen. Clear glass substrate (25) is coated with an opaque coating (30) with multiple holes such as hole (35) made clear into the opaque coating (30). Preferably, holes such as hole (35) are arranged in a repeating array pattern with horizontal and vertical spacing, as well as hole diameter, in a consistent pattern. For example, a preferred embodiment would have holes of 0.001 inch diameter clear zone, spaced 0.002 inches apart, center to center, aligned in an orthogonal pattern. An example of substrate (25) is 0.062 inch thick Schott Glass, and an example of opaque coating (30) is chrome applied by vapor deposition.

Different holes sizes and hole spacing can be used. Preferably, each hole has a diameter of about 0.0001 inch to about 0.01 inch, about 0.0002 inch to about 0.005 inch, or about 0.001 inch. Preferably, the holes are spaced apart by about 0.0002 inch to about 0.02 inch, about 0.0004 inch to about 0.01 inch, or about 0.002 inch. The hole size and hole pattern, in addition to the degree of rotation, are selected to create a Moiré effect.

Coating thicknesses can also vary. Preferable coating thicknesses include about 0.00001 inch to about 0.01 inch, about 0.0025 inch to about 0.0075 inch, or about 0.005 inch.

One or more of the circular apertures can include a lens (lenslet). Preferably, each lenslet has the same positive focal length. In one embodiment, each circular apertures of one array comprises a lens. Such an array is called a Shack-Hartmann Lenslet Array. In another embodiment, both screens are Shack-Hartmann Lenslet Arrays.

The device can further include a beam splitter. Preferably the beam splitter is positioned upstream of the first screen, e.g., between the first screen and a light source. The beam splitter can facilitate directing the light beam, which may be particularly useful when measuring the characteristics of an eye.

Figure 4:
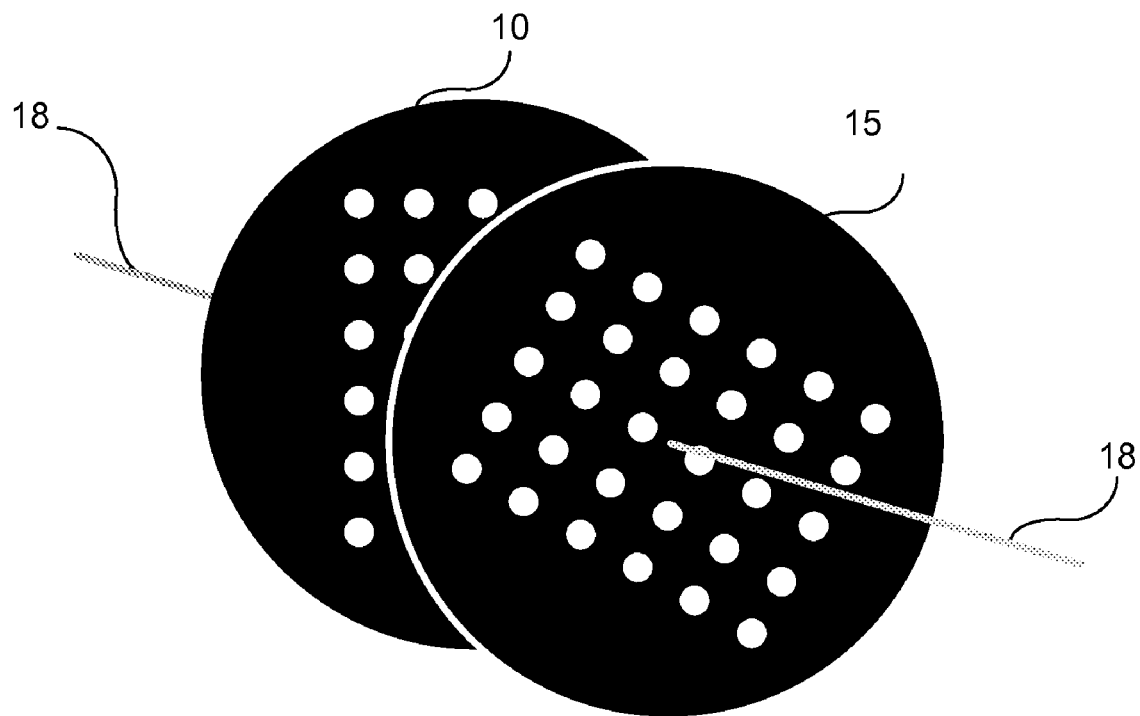
FIG. 4 shows an exemplary rotation orientation of two Hartmann screens.

FIG. 4 shows a perspective view of how the first screen (10) is oriented with respect to the second screen (15), which is a slight rotation to each other. The center of each optic would remain in the same location along the Z axis (18), and the plane of each optic would remain parallel to each other, but the orientation of rotation would occur in the remaining degree of freedom. These terms are known to those skilled in the art of optics design. Furthermore, one of ordinary skill in the art would understand that the screen rotation can also be achieved by rotating the array portion rather than rotating the entire substrate of the screen.

The degree of rotation is sufficient to create a Moiré effect and to create a detectable image of the spots. Preferably, the degree of rotation is about 1 to about 30 degrees, about 3 to about 20 degrees, about 6 to about 18 degrees, about 10 to about 14 degrees, or about 12 degrees.

The rotated screens can be achieved, for example, by the following process: lay the first screen (10) flat on a surface, then lay the second screen (15) flat upon the first screen (10) such that maximum contact surface area is achieved. With both screens still touching, rotate the second screen (15) while maintaining the same amount of contact surface. Then, introduce a distance between the screens during the assembly process, as depicted by FIG. 1.

Figure 5:
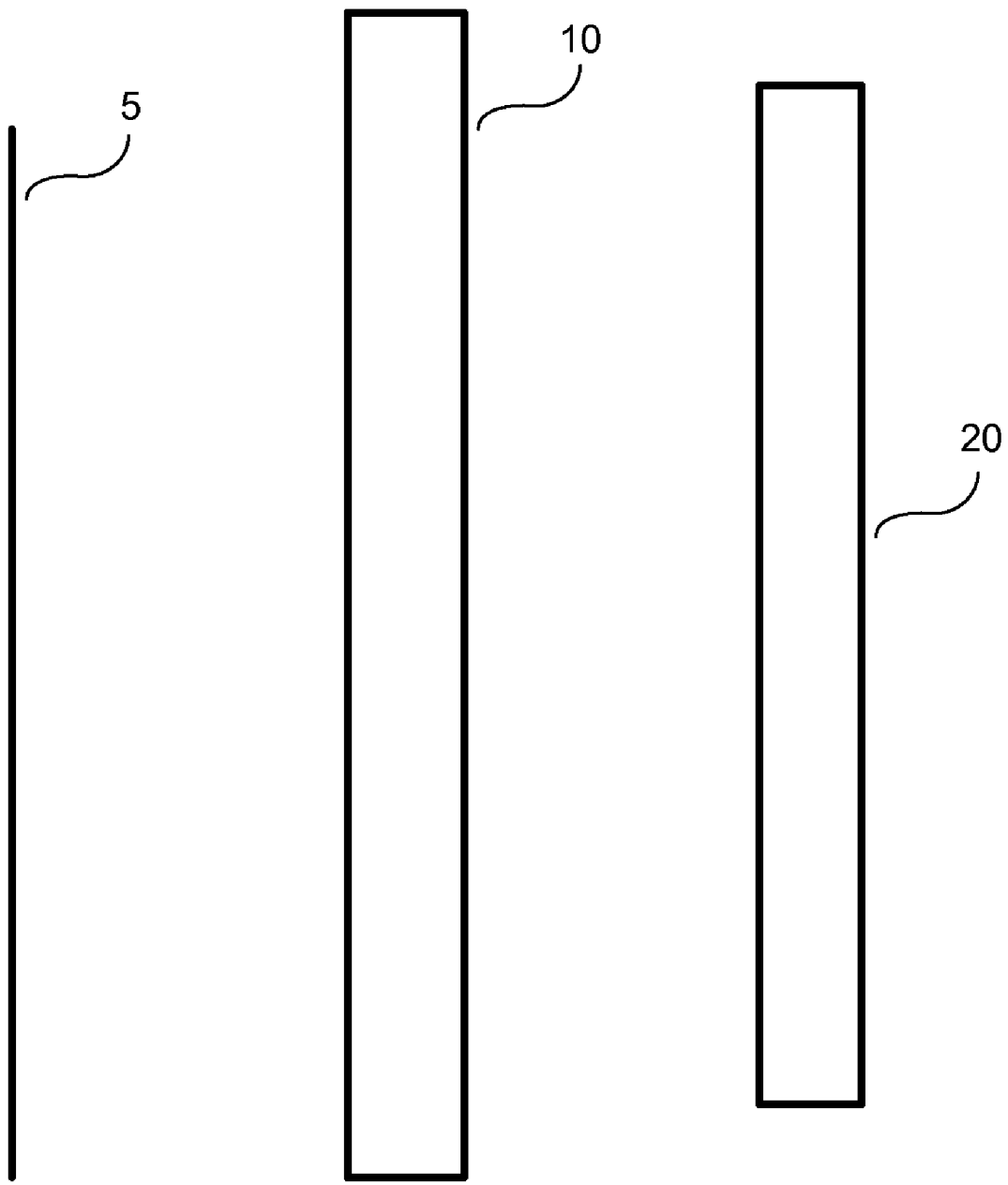
FIG. 5 shows an optical layout for determining the best distance between the two screens.

As shown in FIG. 5, to determine a gap between the first screen (10) and the second screen (15), temporarily remove the second screen (20) and replace it with light detector (20), placing light detector (20) as close as possible to first screen (10). Allow a plane wave of light perpendicular to the Z axis to pass through the first screen (10), then move light detector (20) further and closer away from the first screen (10) while observing the spots being detected by light detector (20). Select a distance between the light detector (20) and the first screen (10) at which distinct spots are being detected by light detector (20). To fine tune the setup, replace plane wave (5) with light of the type and vergence that will be analyzed in the application, and repeat the above distance setting tests. Depending upon conditions, several different distances may be discovered to work well. As a general rule, longer distances provide higher sensitivity, and closer distances provide higher dynamic range of measurement. Also, one distance may provide more dynamic range in one direction of vergence or divergence measurement, while another may provide more dynamic range in the opposite direction of vergence or divergence. After a suitable distance is selected, remove the light detector (20), and replace it with the second screen (15) at the distance and location selected, as described above. Replace light detector (20) at its appropriate position described in FIG. 1 or FIG. 2.

Once assembled in this configuration, further distances and rotation angles may be tested by moving first screen (10) and second screen (15) so that the two surfaces with the etched holes are in contact with each other, and some angle between the two is selected, such as 3 degrees. Then place within the beam of light, before it is incident upon first screen (10), a lens with a 200 mm positive focal length (i.e., 5 Diopters), and observe that there is no movement of the spots. Then, slowly move the first screen (10) away from second screen (15) while placing into the beam and then removing from the beam the 200 mm positive focal length lens and observing the movement of the spots at each distance between the two screens. As first screen (10) moves further away from second screen (15), the amount of movement of the spots will increase (i.e., the system will become more sensitive to the light angle). Once a desired distance is selected, the rotation of the two screens may be adjusted. As the angle between the two screens increases, the density of the spot pattern in increases, but the amount of movement of the spots per diopter of light angle will decrease. FIGS. 14-21 show the variation in spot pattern density under various rotations. During these various setup conditions, one can expose the setup to a range of light conditions expected to be seen during use and select the setup conditions that produces the combination of the most distinct spot patterns coupled with the amount of movement of spots per diopter of light vergence or divergence that will best yield the required sensitivity.

Of the many possible configurations, one exemplary setup that works when analyzing light beams in the central portion of the visible spectrum (e.g., green at 532 nm) is to have first and second screens, flat surfaces parallel to each other but rotated 12 degrees to each other, each having 0.001428 inch diameter holes spaced 0.002857 inches apart, center to center, with an optical distance of 0.024 of an inch between the first and second screens, and the light detector (e.g., a camera) set up to image the plane of where the holes are on the second screen.

The image quality achieved by the Hartmann-Moiré system can advantageously surpass the image quality achieved by a Talbot-Moiré system. The amount of spot movement in the Hartmann-Moiré system is directly proportional to the refractive power being observed by the system. However, the Talbot-Moiré system requires that the second Talbot optic be placed at a specific, calculated distance away from the first Talbot optic, described by the following formula: Distance=period squared divided by the wavelength of the light. The period is the distance between the holes. In the example described in the preceding paragraph, the second Talbot optic must be placed 0.097 inch away from the first Talbot optic, and it will not function properly if it is any closer. In contrast, Hartmann screens can be placed much closer to one another and at many more locations where it will operate properly.

The distance between screens in a Hartmann-based system is not constrained by this Talbot formula, proving that it works under a different set of principles of physics. The Hartmann-Moiré system described herein will work at the same distance that the Talbot-Moiré formula prescribes, but it also works at many other distances that would not work with Talbot-Moiré system. This flexibility of distances allows measurements of a wider spectrum of light wavelength. Also, a smaller distance between screens can be used with the Hartmann-Moiré system. This can be quite useful in optical applications wherein the observer or camera must simultaneously view the image of an eye and the spot pattern. The image of the eye comes into focus at the first screen, but the spots are in focus at the second screen, which is where the camera focuses. If the distance between the two screens is too great, the eye becomes out of focus to the camera. When this distance can be made shorter, as in the present system, then the image of the eye formed at the first screen can be in better focus to the camera that is focused at the second screen, providing a compound image of both the eye and the spots, with the spots superimposed over the eye image. This allows for a more precise determination of the refractive power of the eye at each particular spot location because each spot can be associated with a particular corresponding location of the eye.

In one embodiment, the invention provides a large dynamic range of measurement and/or a high level of sensitivity to measure smaller wavefront slopes. Preferably, the invention provides both a large dynamic range of measurement and a high level of sensitivity to measure smaller wavefront slopes. In particular, the invention can be configured to provide a measurement accurate within about 0.5 D, 0.4 D, 0.3 D, 0.25 D, 0.23 D, 0.2 D, or 0.1 D over a range of about 5 D, 7 D, 10 D, 11 D, 15 D, 16 D, 17 D, 18 D, 20 D, 24 D, 30 D, 35 D, 38D, or 40 D, or other increments within these ranges.

With experimental trials, varying one or more variable at a time—optical configuration, array pattern, hole size, hole spacing, hole location, screen spacing, screen materials, screen rotation angles, light wavelength, light detector type, etc.—will produce various densities and response rates of movement of the spots, and an appropriate combination can be selected to best suit the particular application.

Figure 6:
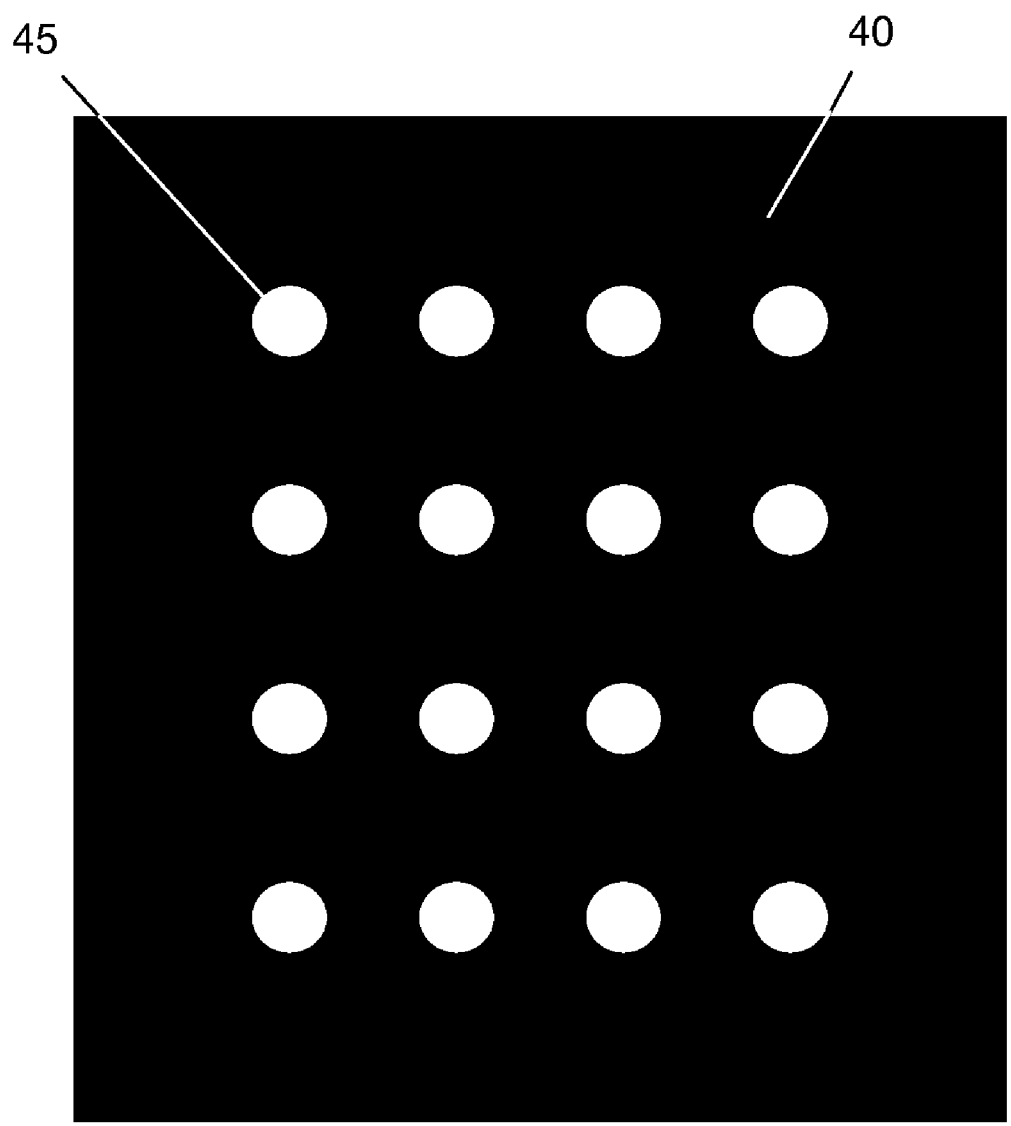
FIG. 6 shows an exemplary spot pattern created by a plane light wave passing through the layout depicted by FIG. 1.

FIG. 6 shows a field of view (40) (the image that light detector (20) produces) having an exemplary array of spots produced by a planar wave of light that passed through both screens. The distance between all of the spots increases as the relative rotation angle between the first screen and the second screen decreases in angle, and the distance decreases as the rotation increases. Example spot (45) is shown in an example location. The location of each spot is recorded with a known beam of light being examined by the entire device. Each spot of light will move in direction and magnitude in relation to the change of the slope of the light that has passed through the device in the zone being represented by that spot. In other words, if all the spots move uniformly, the entire beam of light possesses the same change in slope across it, in a uniform pattern. If some spots move more or less than others, that indicates a more or less change of slope for the area that that particular spot represents.

One of ordinary skill in the art, e.g., one familiar with Machine Vision and computer programming, knows how to instruct a computer to measure the movement of the spots. Commercially available programs such as Matlab, or other available source code for spot centering, provide such routines.

Figure 7:
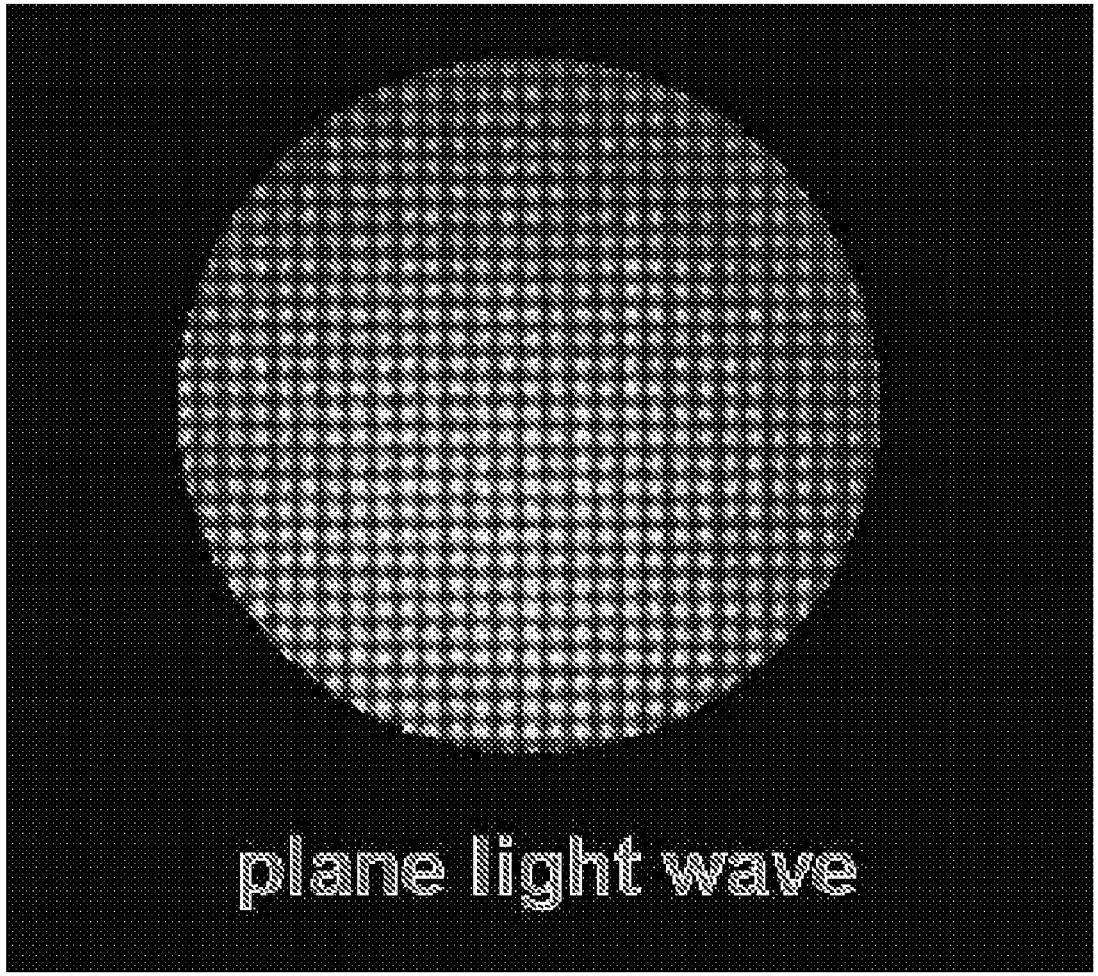
FIG. 7 shows a Point Grey FL2 CCD camera photograph of the exemplary spot pattern created by a plane light wave passing through the layout depicted by FIG. 1.
Figure 8:
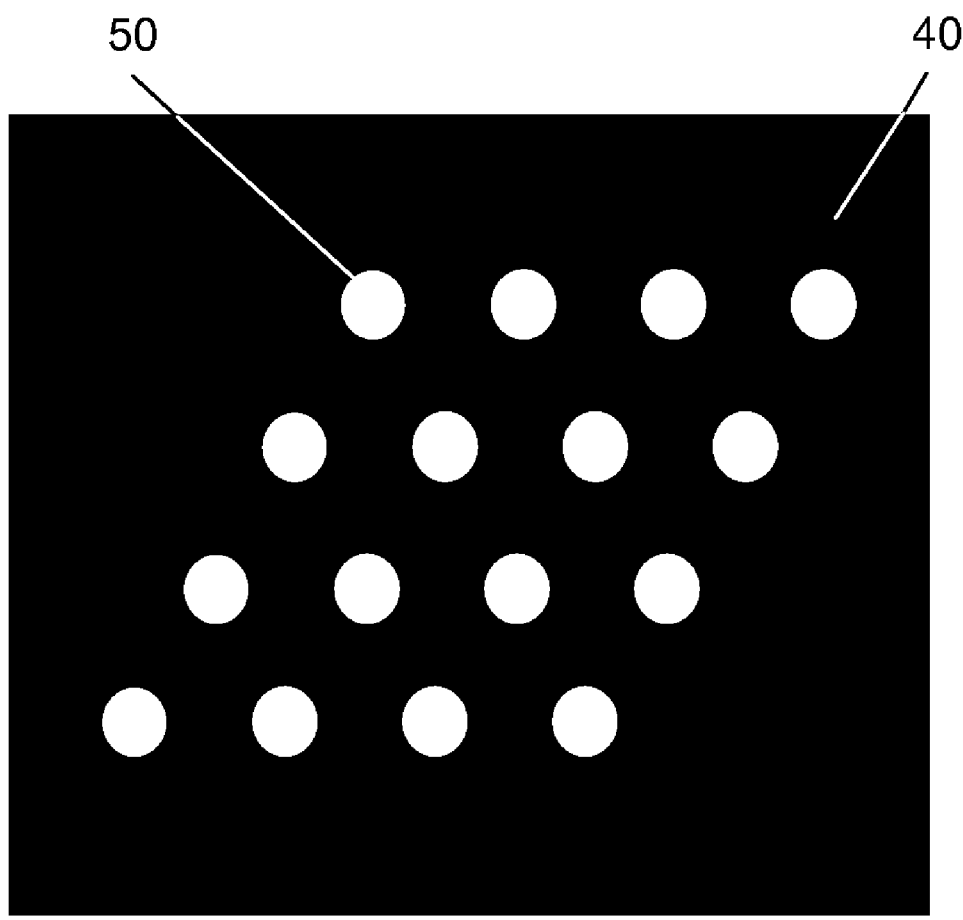
FIG. 8 shows an exemplary spot pattern created by a cylindrical light wave passing through the layout depicted by FIG. 1.
Figure 9:
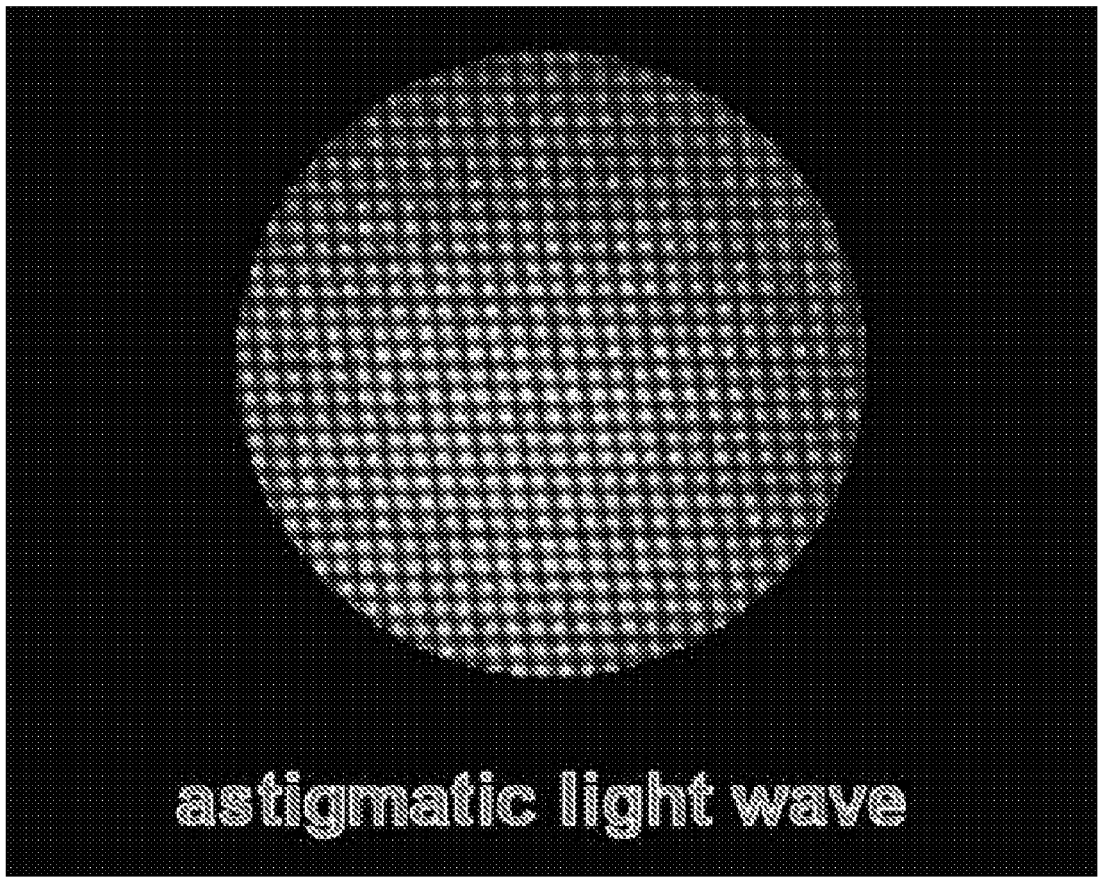
FIG. 9 shows a Point Grey FL2 CCD camera photograph of the exemplary spot pattern created by a cylindrical light wave (i.e., the beam has an astigmatism) passing through the layout depicted by FIG. 1.

If the planar light beam used in FIGS. 6 and 7 is replaced with a light beam having an astigmatism, the spot would move to a new location as shown by example spot (50) in FIGS. 8 and 9. The pattern of spots in the field of view (40) shown in FIG. 8 is an example of pure cylinder deviation, which is a term understood by those skilled in the art of optics design.

Figure 10:
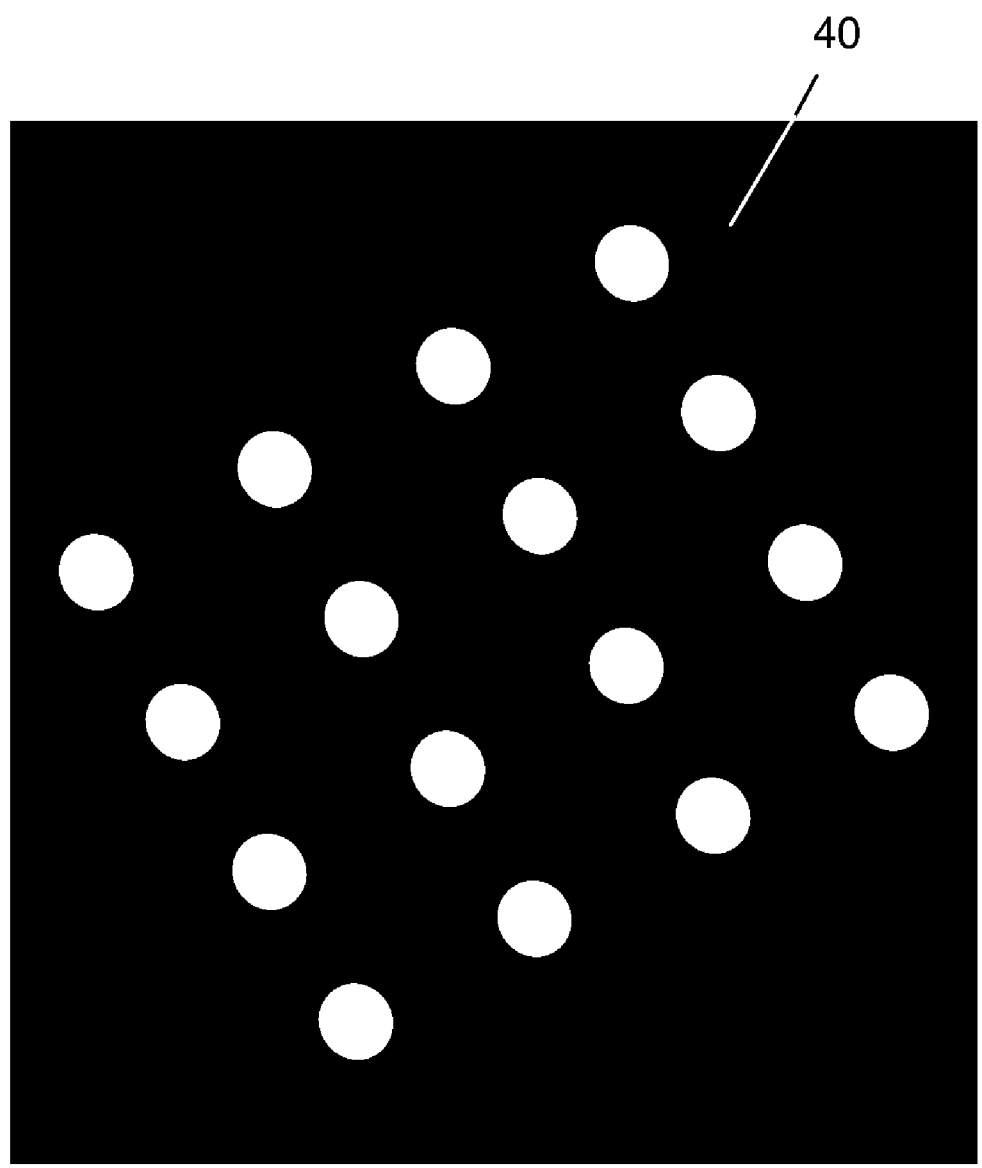
FIG. 10 shows an exemplary spot pattern created by a purely spherical light wave passing through the layout depicted by FIG. 1.
Figure 11:
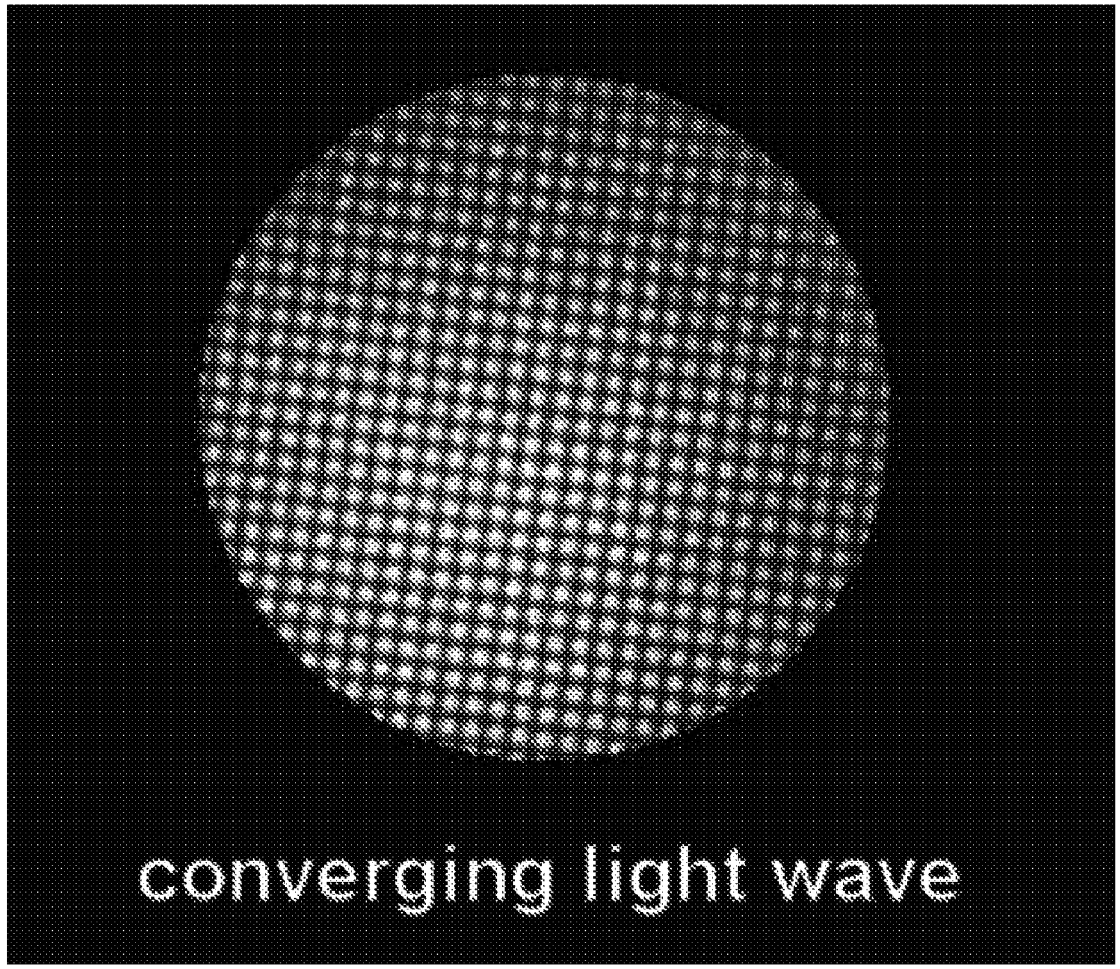
FIG. 11 shows a Point Grey FL2 CCD camera photograph of the exemplary spot pattern created by a converging light wave passing through the layout depicted by FIG. 1.
Figure 12:
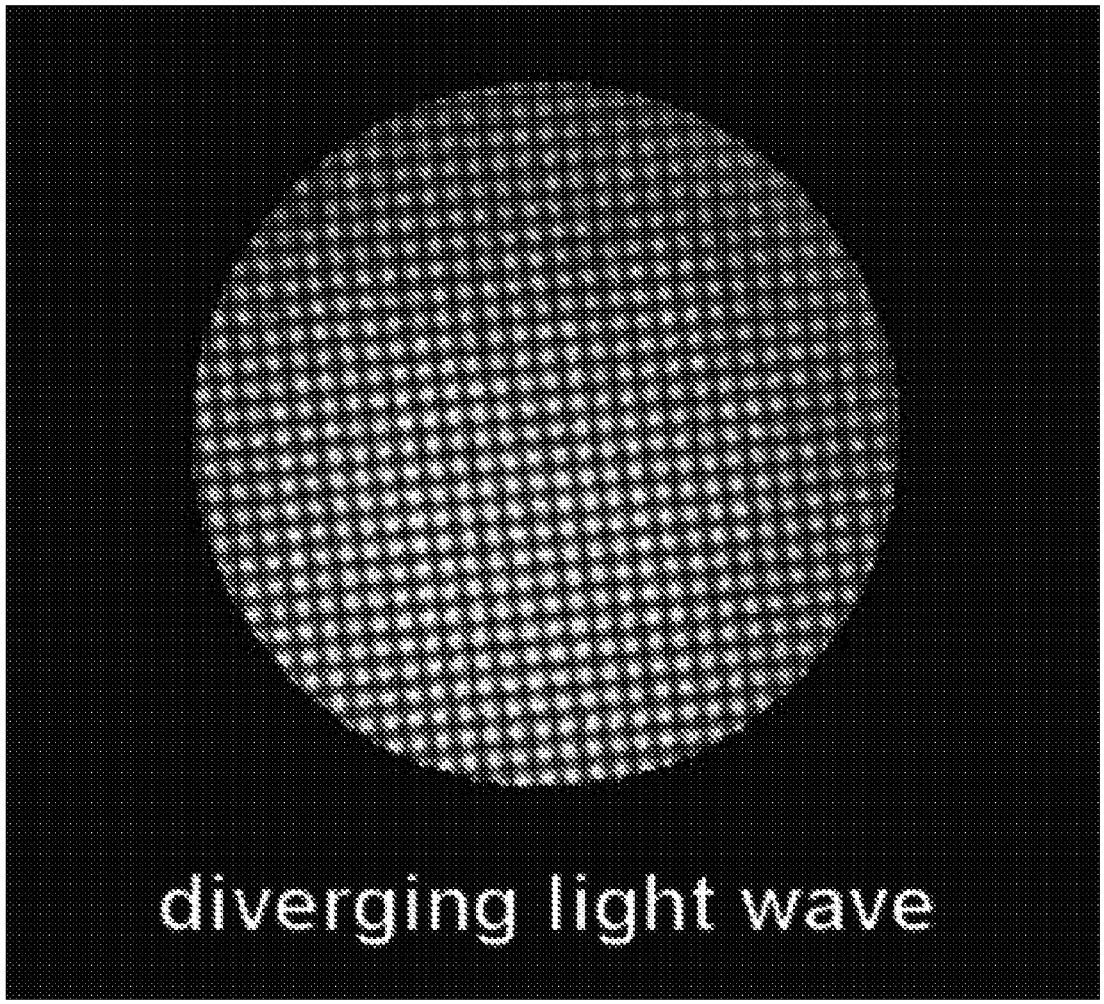
FIG. 12 shows a Point Grey FL2 CCD camera photograph of the exemplary spot pattern created by a diverging light wave passing through the layout depicted by FIG. 1.

If the planar light beam used in FIGS. 6 and 7 is replaced with a light beam having a purely spherical change to its slope, the exemplary spot pattern would appear as in FIGS. 10-12.

Figure 13:
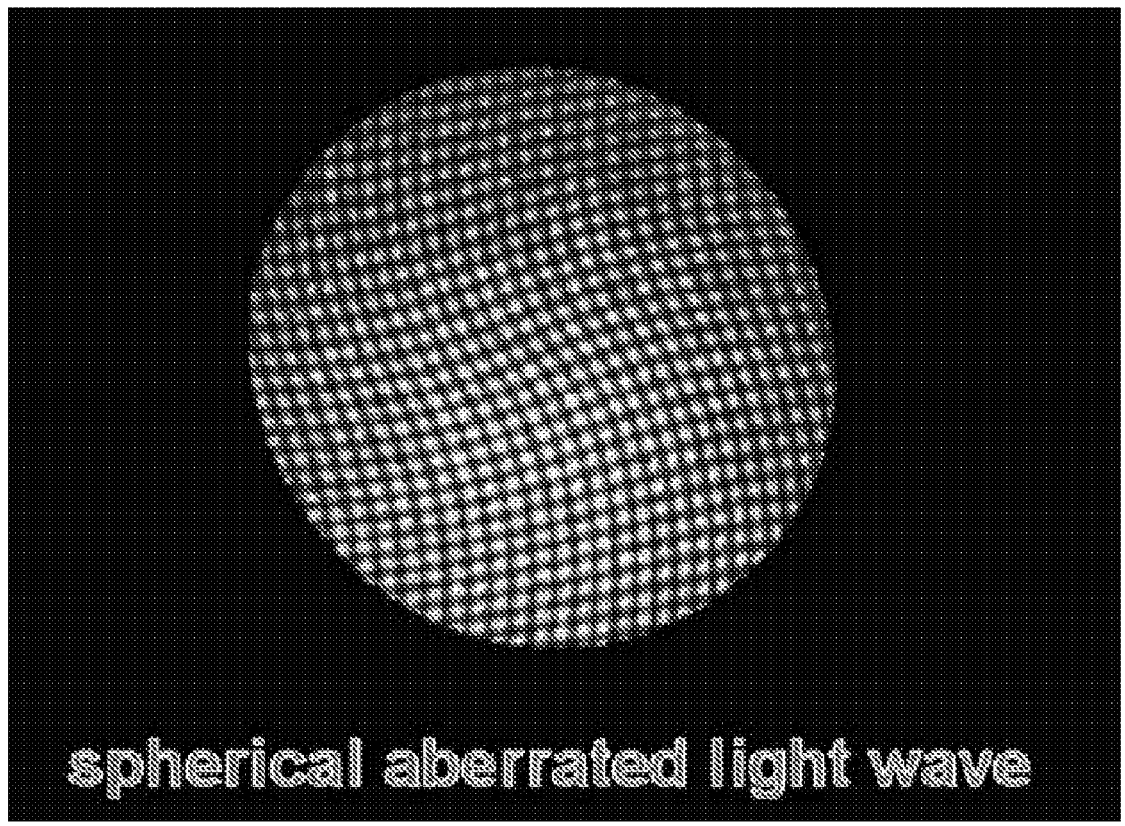
FIG. 13 shows a Point Grey FL2 CCD camera photograph of the exemplary spot pattern created by a spherical aberrated light wave passing through the layout depicted by FIG. 1.
Figure 14:
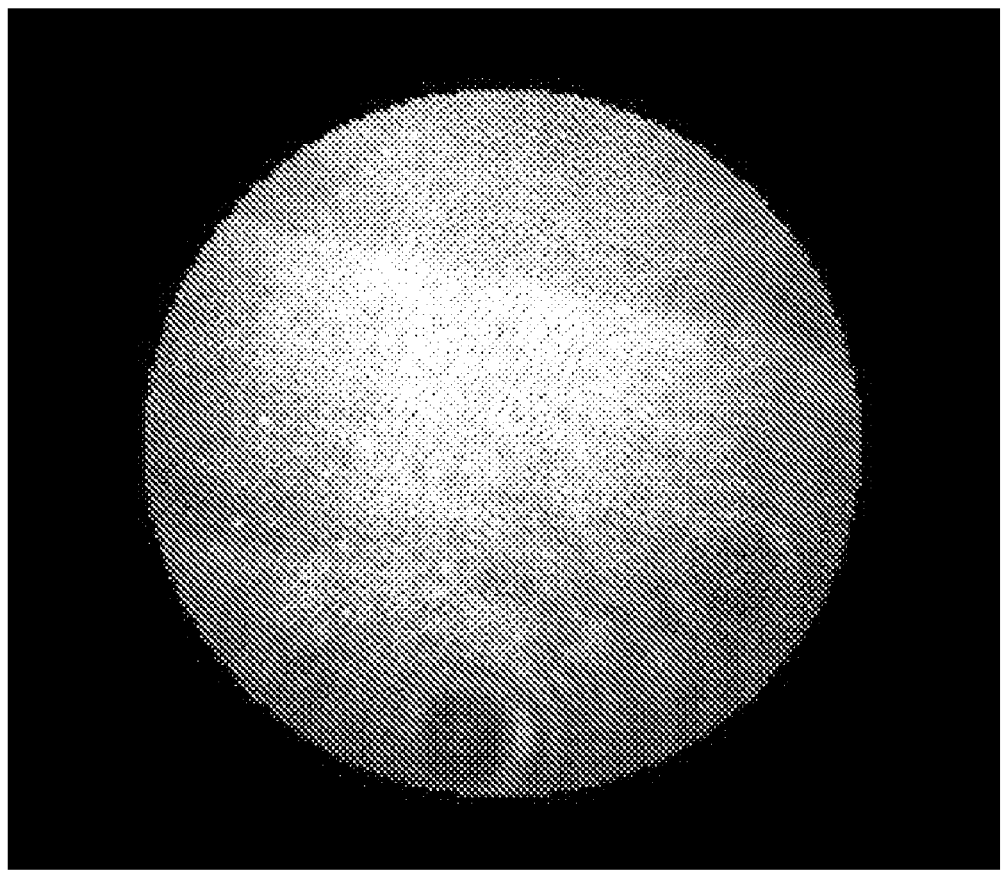
FIG. 14 shows a Point Grey FL2 CCD camera photograph of the image formed when two Hartmann screens are positioned at zero degrees rotation.
Figure 15:
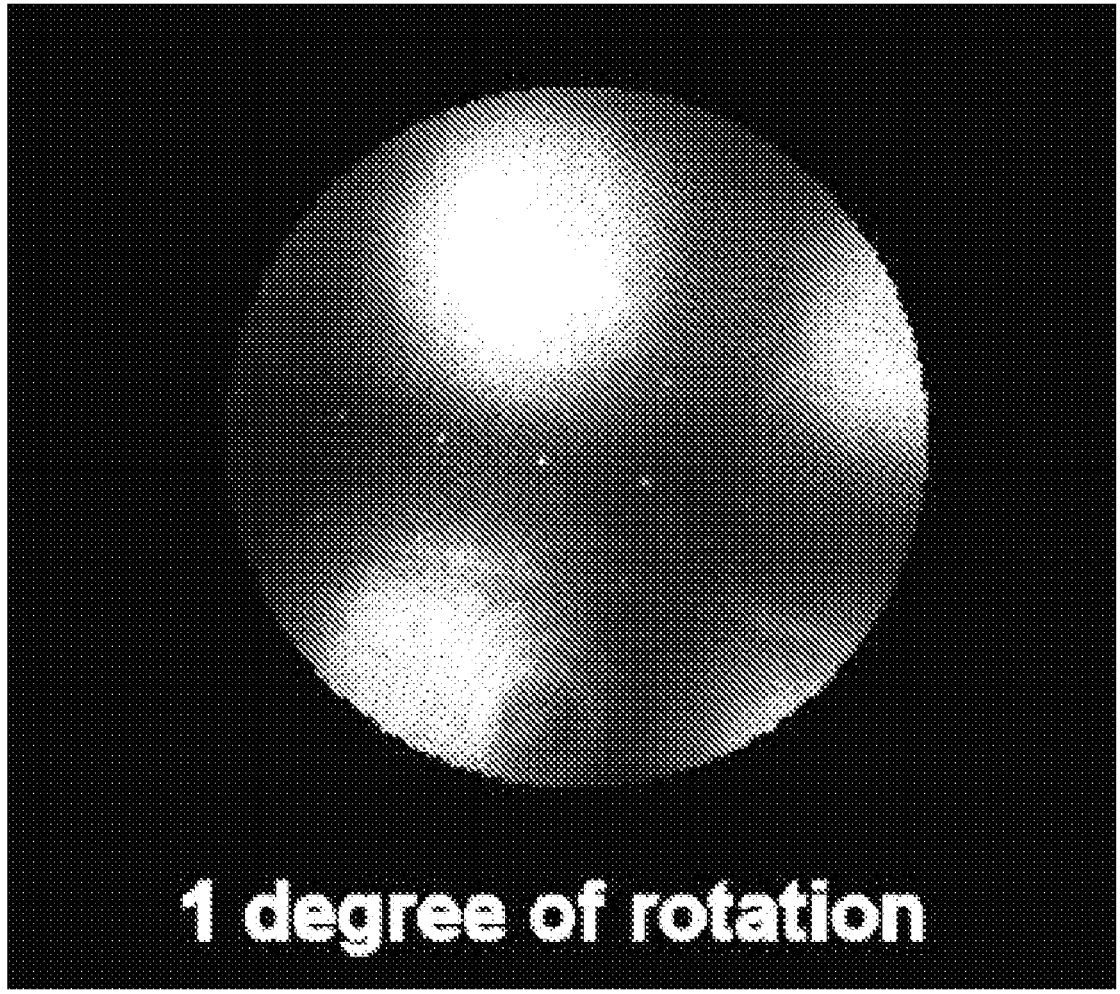
FIG. 15 shows a Point Grey FL2 CCD camera photograph of the image formed when two Hartmann screens are positioned at one degree rotation.
Figure 16:
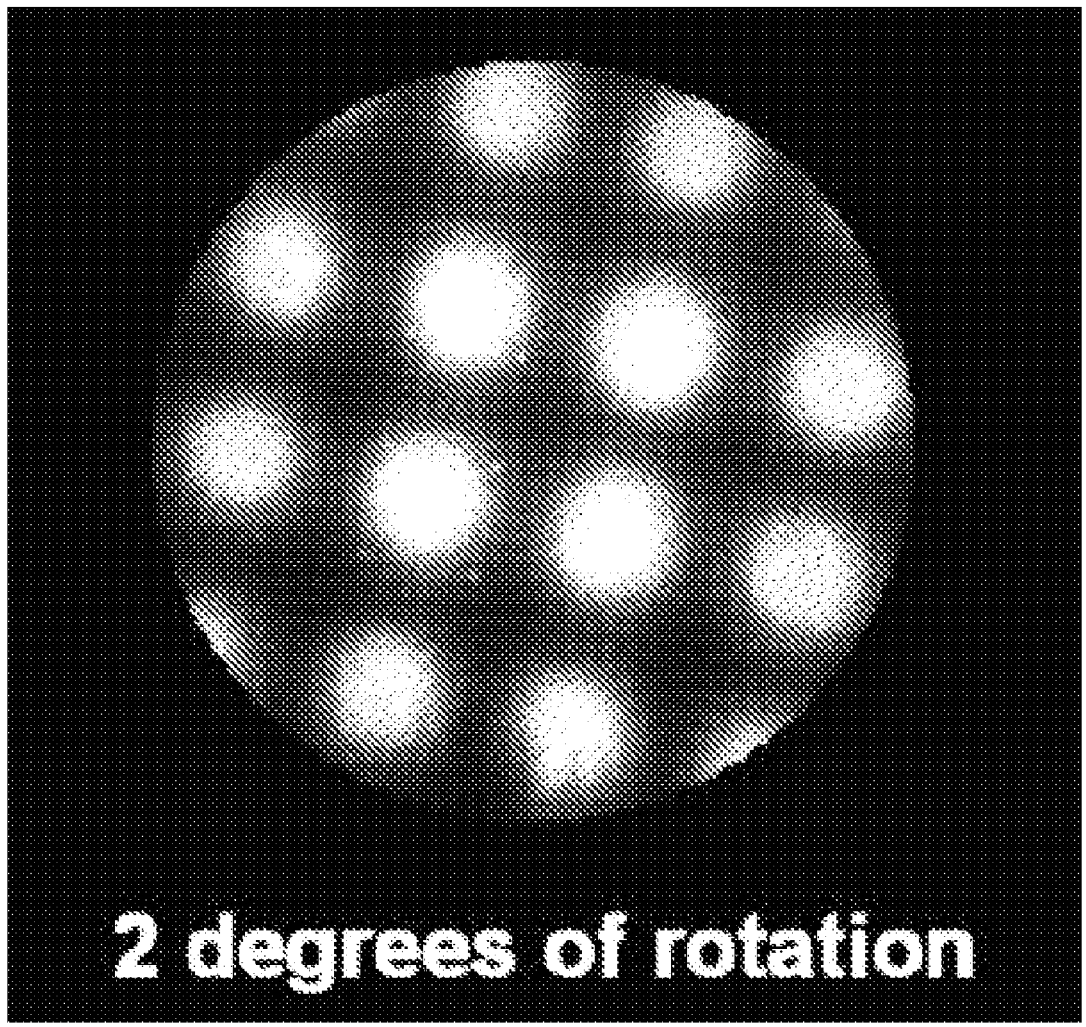
FIG. 16 shows a Point Grey FL2 CCD camera photograph of the image formed when two Hartmann screens are positioned at two degrees rotation.
Figure 17:
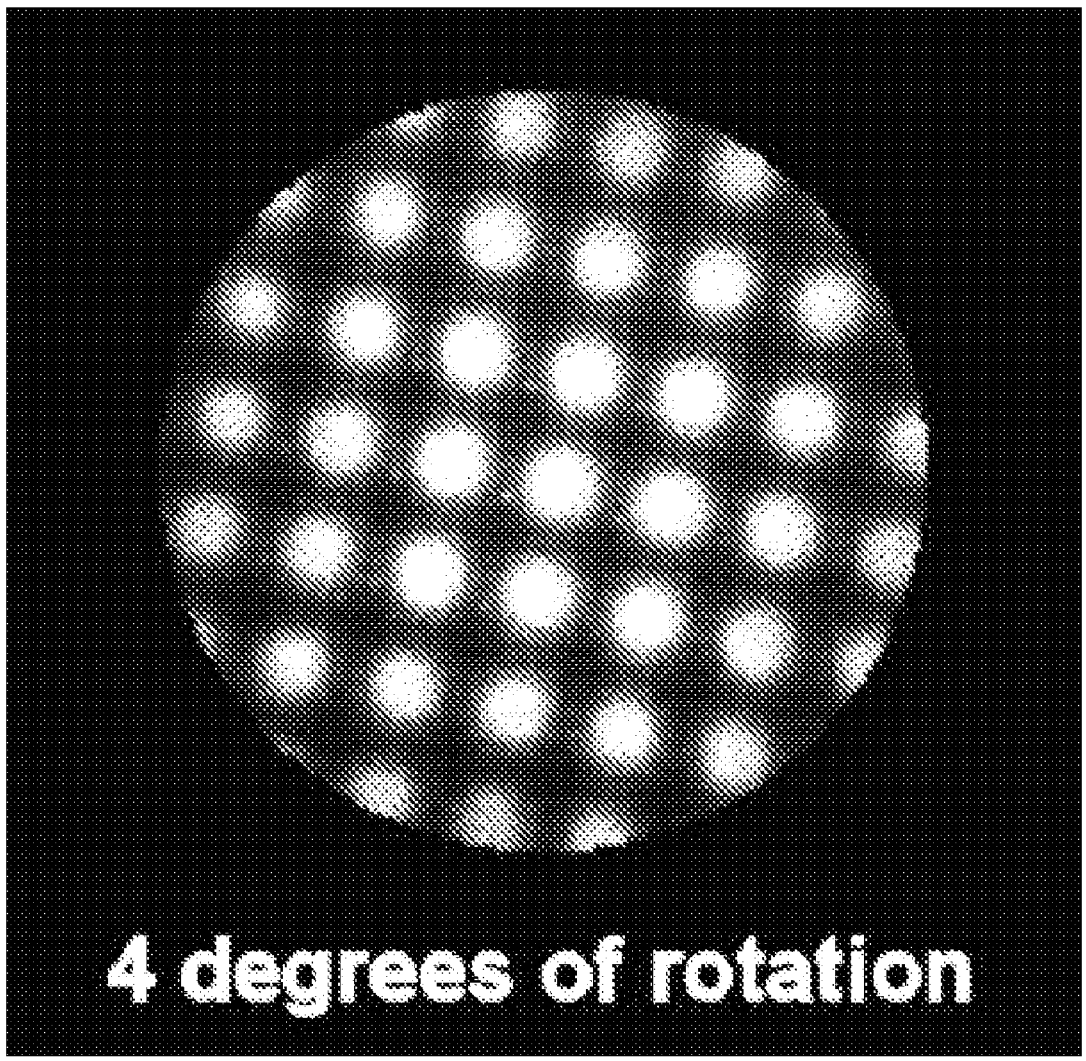
FIG. 17 shows a Point Grey FL2 CCD camera photograph of the image formed when two Hartmann screens are positioned at four degrees rotation.
Figure 18:
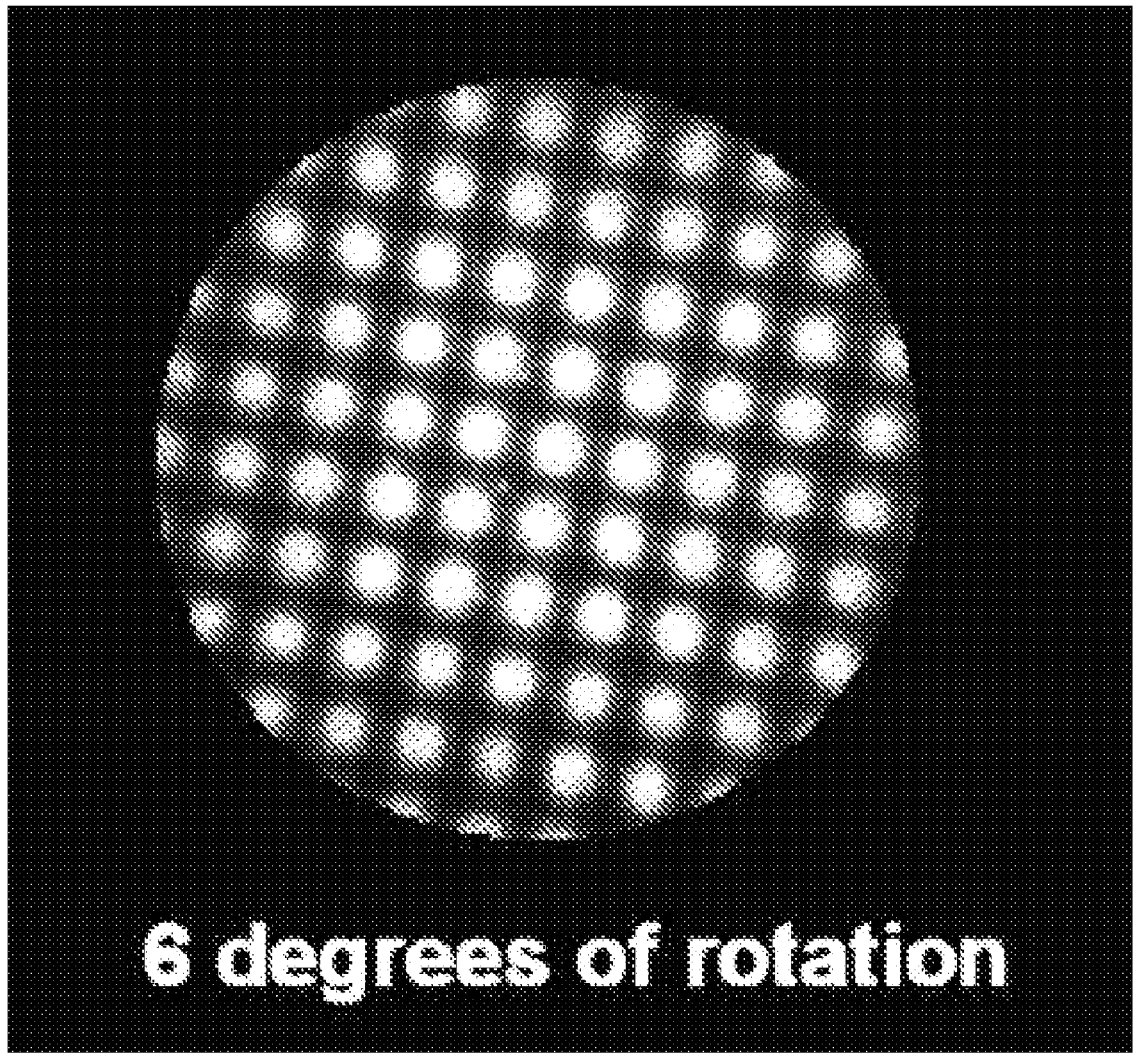
FIG. 18 shows a Point Grey FL2 CCD camera photograph of the image formed when two Hartmann screens are positioned at six degrees rotation.
Figure 19:
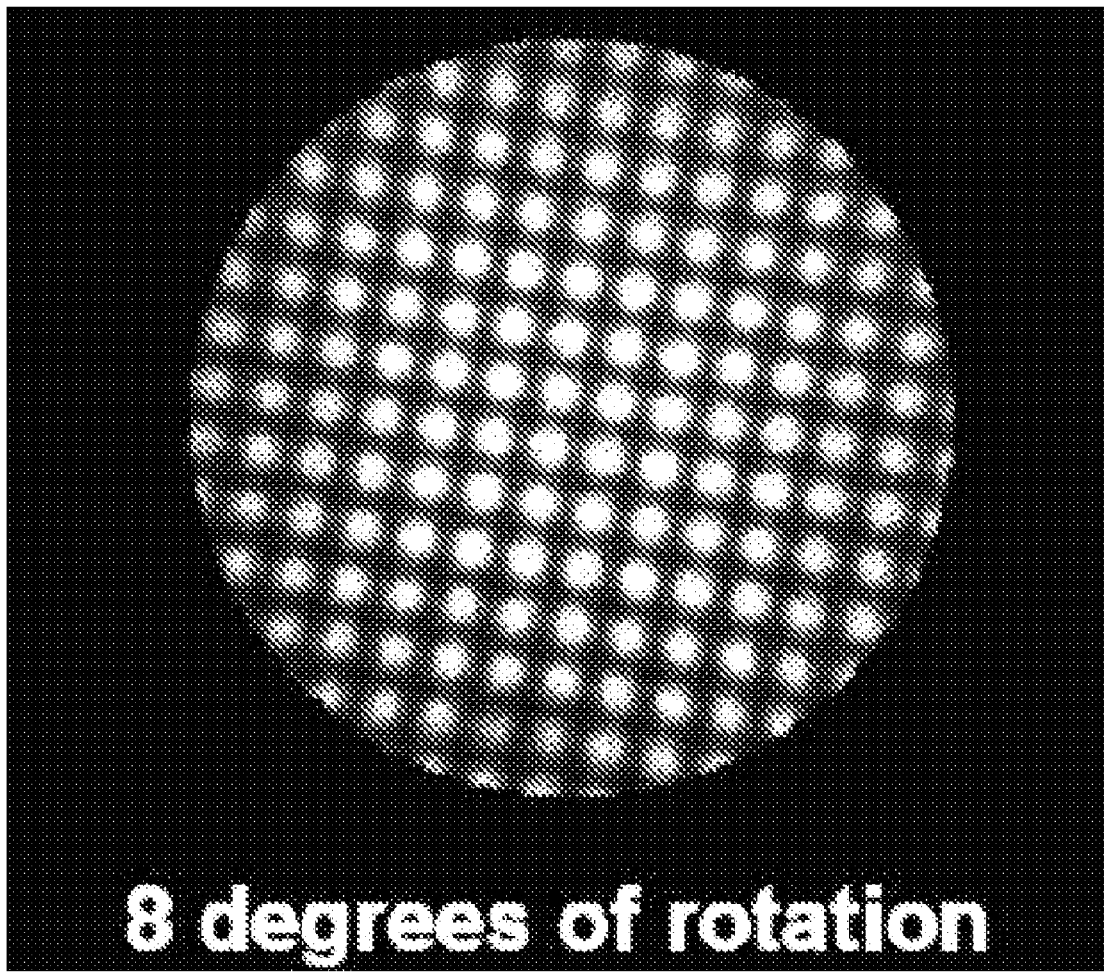
FIG. 19 shows a Point Grey FL2 CCD camera photograph of the image formed when two Hartmann screens are positioned at eight degrees rotation.
Figure 20:
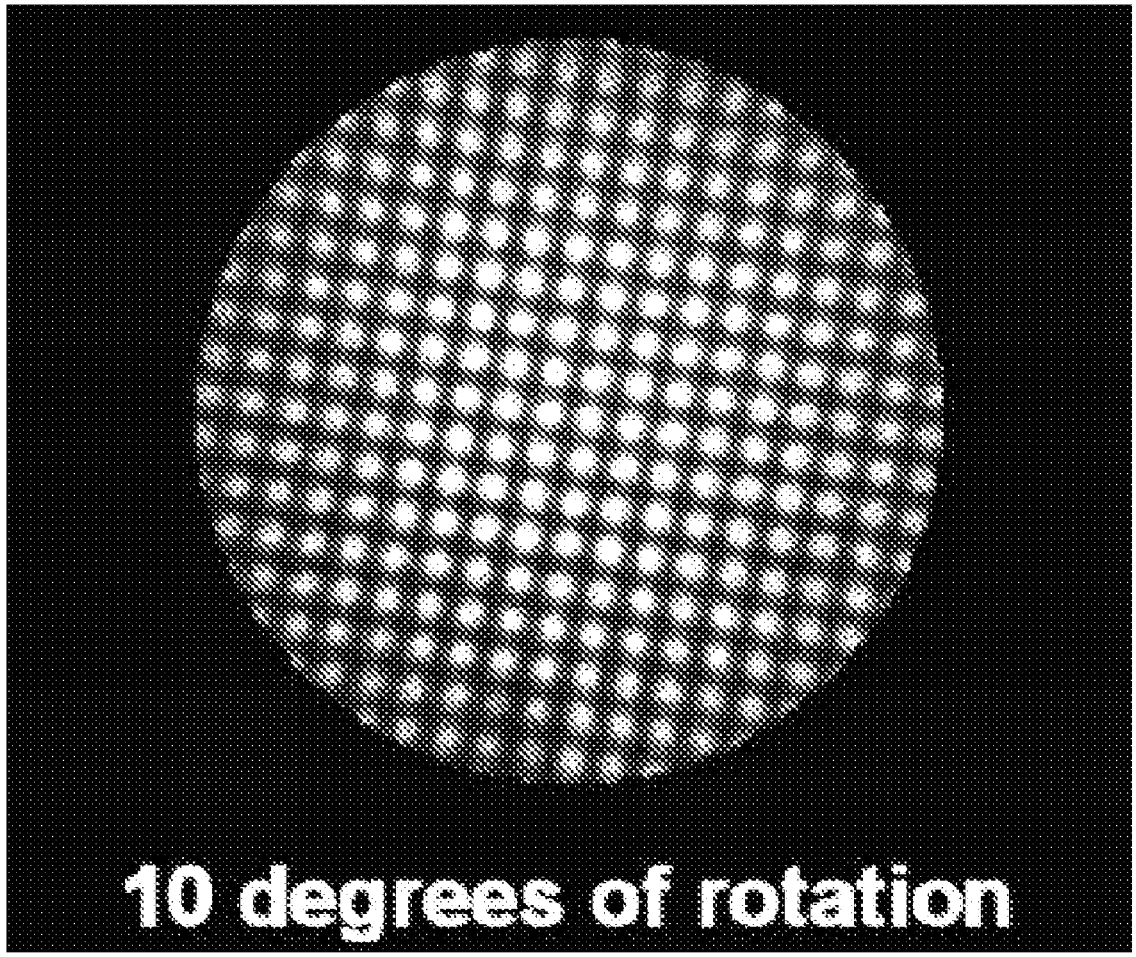
FIG. 20 shows a Point Grey FL2 CCD camera photograph of the image formed when two Hartmann screens are positioned at ten degrees rotation.
Figure 21:
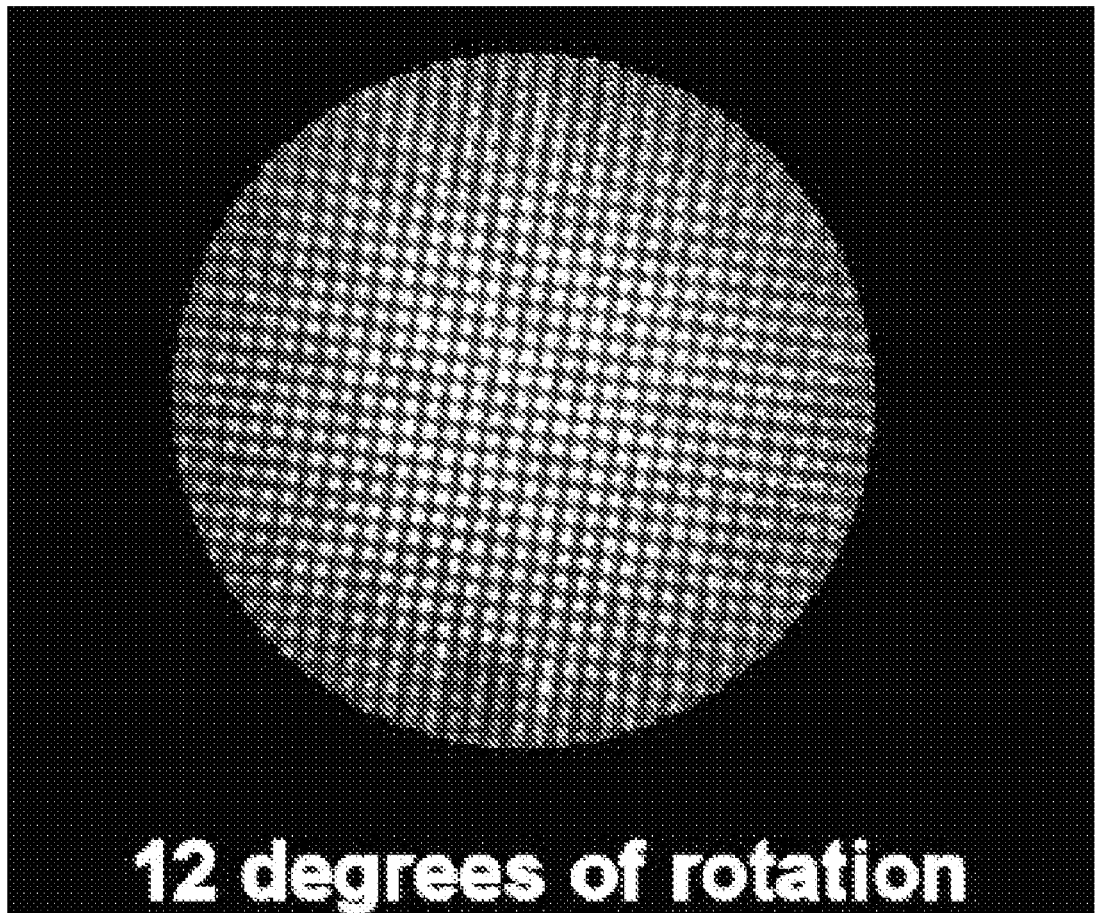
FIG. 21 shows a Point Grey FL2 CCD camera photograph of the image formed when two Hartmann screens are positioned at twelve degrees rotation.

If the planar light beam used in FIGS. 6 and 7 is replaced with a light beam having spherical aberration in its slope, the exemplary spot pattern would appear as in FIG. 13.

To calibrate the system, the preferred method is to pass a plane wave of light through the system and record the location of all the spots. Then pass a series of different light beams through the system with known amounts of sphere and cylinder changes, and record the movement of each of the spots at each location under each light beam condition. From this calibration, the relationship of the movement of the spots to the slope change of the light beam being analyzed can be quantified, then used for the computation step when the device is used in service. One of ordinary skill in the art of optics design knows how to create various optical wavefronts for this calibration method. One way to do so would be to purchase a 25 mm diameter collimated laser beam from such suppliers as Newport Optics, Melles Griot, or Thor Labs, and then purchase an Optometrists Trial Lens set from any ophthalmic or optometric supplier such as Reichert, American Optical, or other vendors, then place these trial lenses within the laser beam.

The device described above can be used to measure the slope of a wavefront. The device can be used in a variety of optical applications, such as measuring the characteristics of a lens, including an eye. A method of measuring characteristics of a lens comprises: directing light into the lens; directing the light from the lens through a first screen comprising a first two-dimensional array of circular apertures; directing the light from the first screen through a second screen comprising a second two-dimensional array of circular apertures, wherein the second screen is placed downstream of the first screen, the second screen is in a plane parallel to the first screen, and the second screen is rotated relative to the first screen; and detecting the light from the second screen at a light detector. Similarly, the device can be used to measure the characteristics of an eye by first directing light, e.g., a small diameter beam of light, into an eye. The eye reflects the beam out, and then the reflected beam is directed into the first and second two-dimensional arrays and a light detector. These methods can be used with any of the device embodiments described herein.

The present invention is further described by the following non-limiting examples.

EXAMPLE 1

Testing the Wavefront Sensor with Spherical and Cylindrical Trial Lenses

Figure 22:
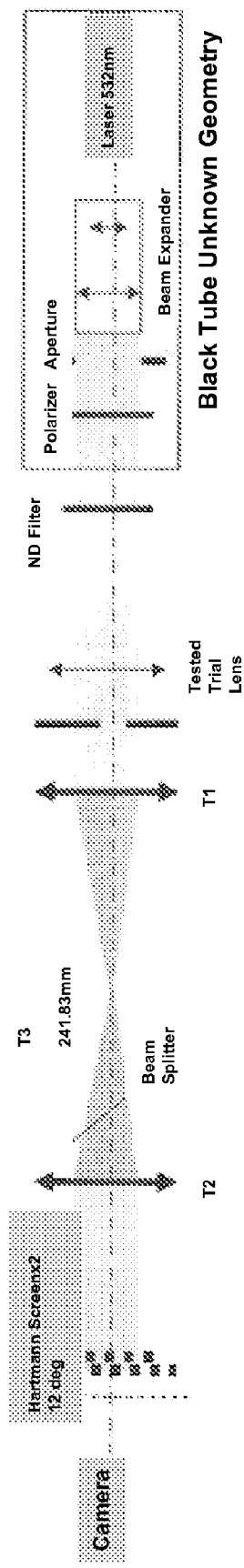
FIG. 22 show an exemplary test configuration for Topcon trial lenses.

Data were measured at a wavelength of 532 nm without focus adjustment so that the full range of wavefront vergences was presented to the wavefront sensor. The accuracy and dynamic range of the Hartmann-Moiré wavefront sensor was evaluated by measuring defocus and astigmatism induced by a series of standard Topcon spherical lenses (e.g., 77 lenses from −20 D to +18 D) and cylindrical trial lenses (e.g., 16 lenses from −8 D to 8 D). Repeatability of the Hartmann-Moiré instrument was assessed by taking 3 repeated measurements within a 2-minute period. Measured trial lens values with the Hartmann-Moiré wavefront sensor were compared to lens values verified with a standard lensometer. Analyses were based on a 4-mm pupil diameter specified in the software. The test configuration is shown in FIG. 22.

Figure 23:
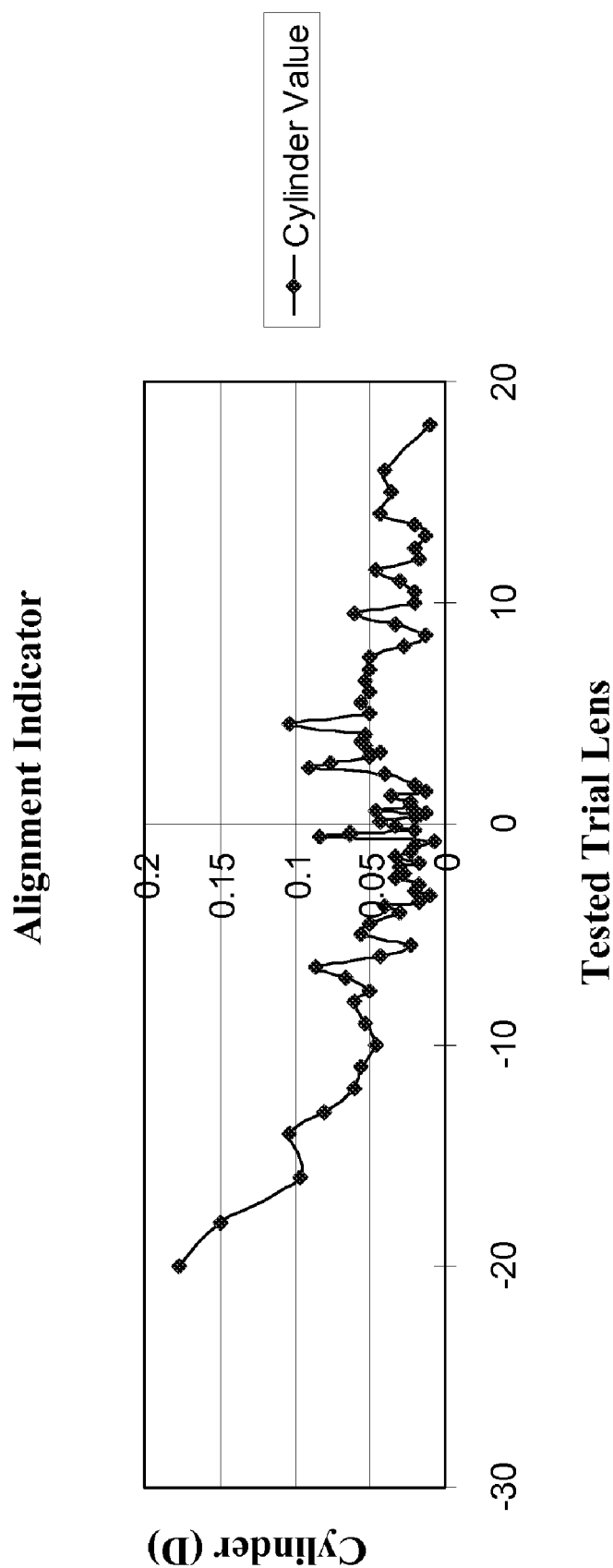
FIG. 23 shows measurements to assure tight alignment tolerance for the testing of trial lenses. The amount of measured cylinder was measured using a sphere lens from about −20 D to +18 D with fixed scheme.
Figure 24:
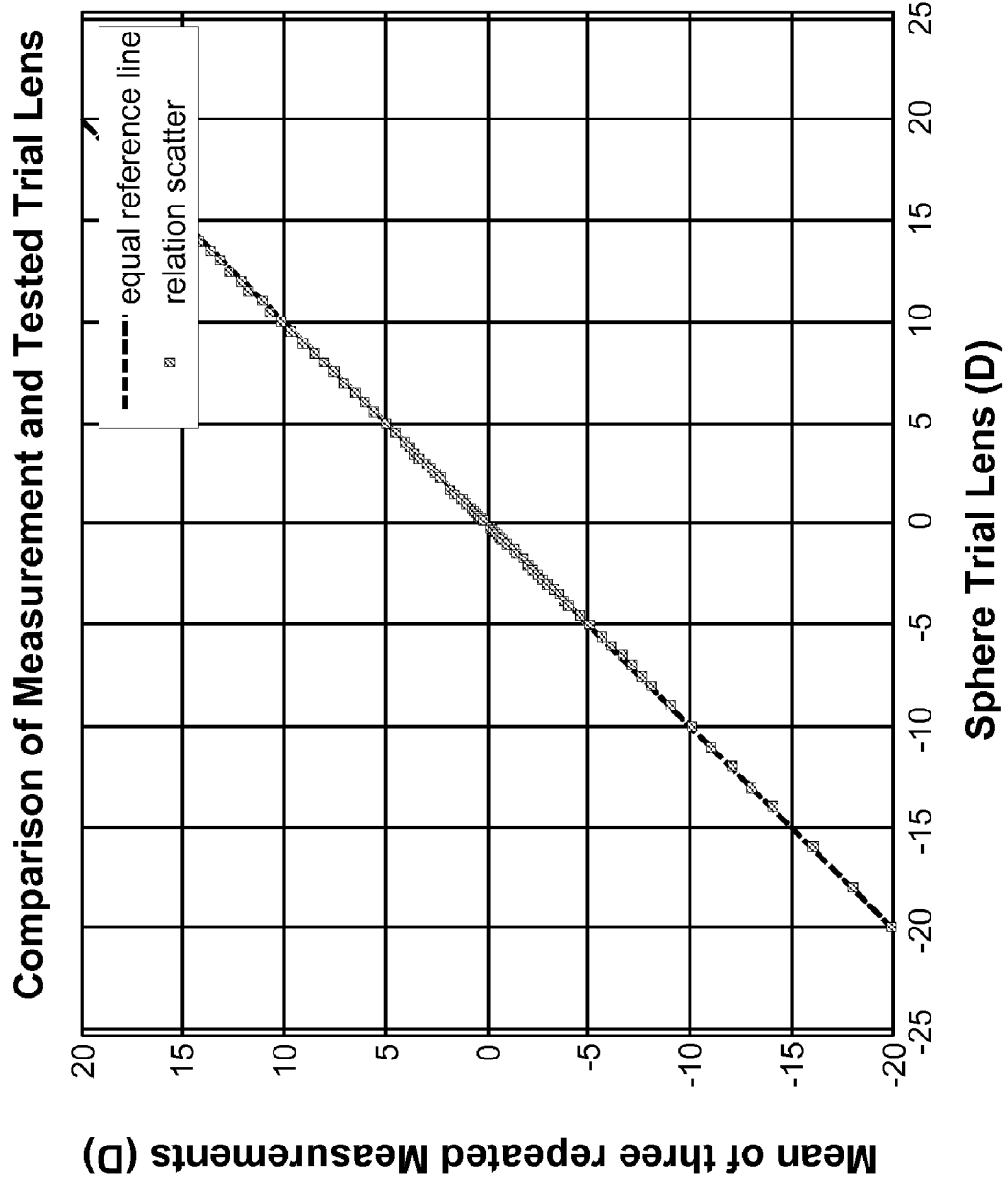
FIG. 24 shows the results of a comparison of measurement and tested trial lenses for spherical test lenses from −20 D to +18 D (correlation coefficient r=1.000). From −0.75 D to +0.75 D, the increments of the test lenses was 0.125 D.
Figure 25:
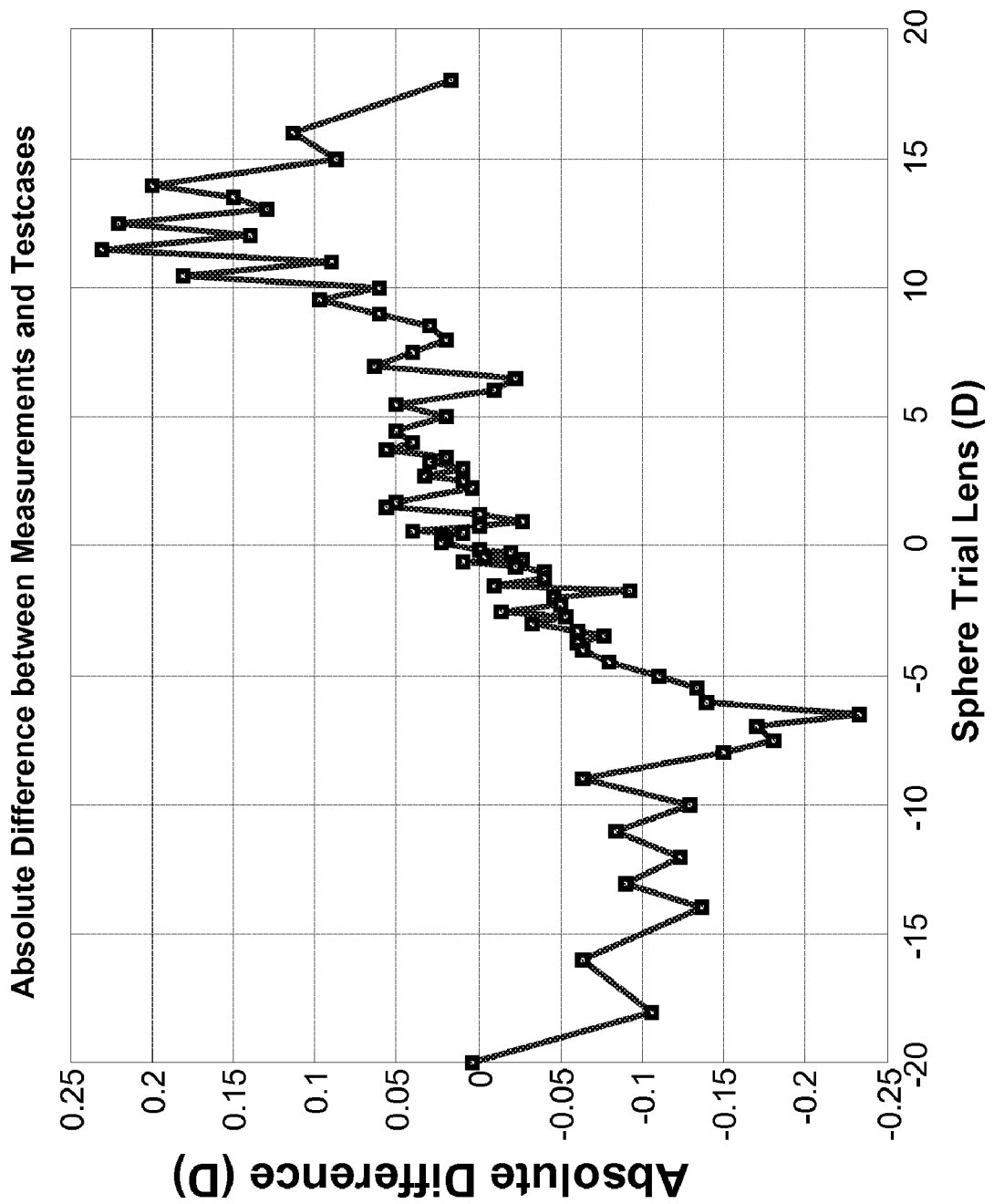
FIG. 25 shows the results of absolute difference between measurements and test lenses for spherical test lenses from −20 D to +18 D (Absolute mean difference: 0.0682 D, Maximum difference: 0.23 D).
Figure 26:
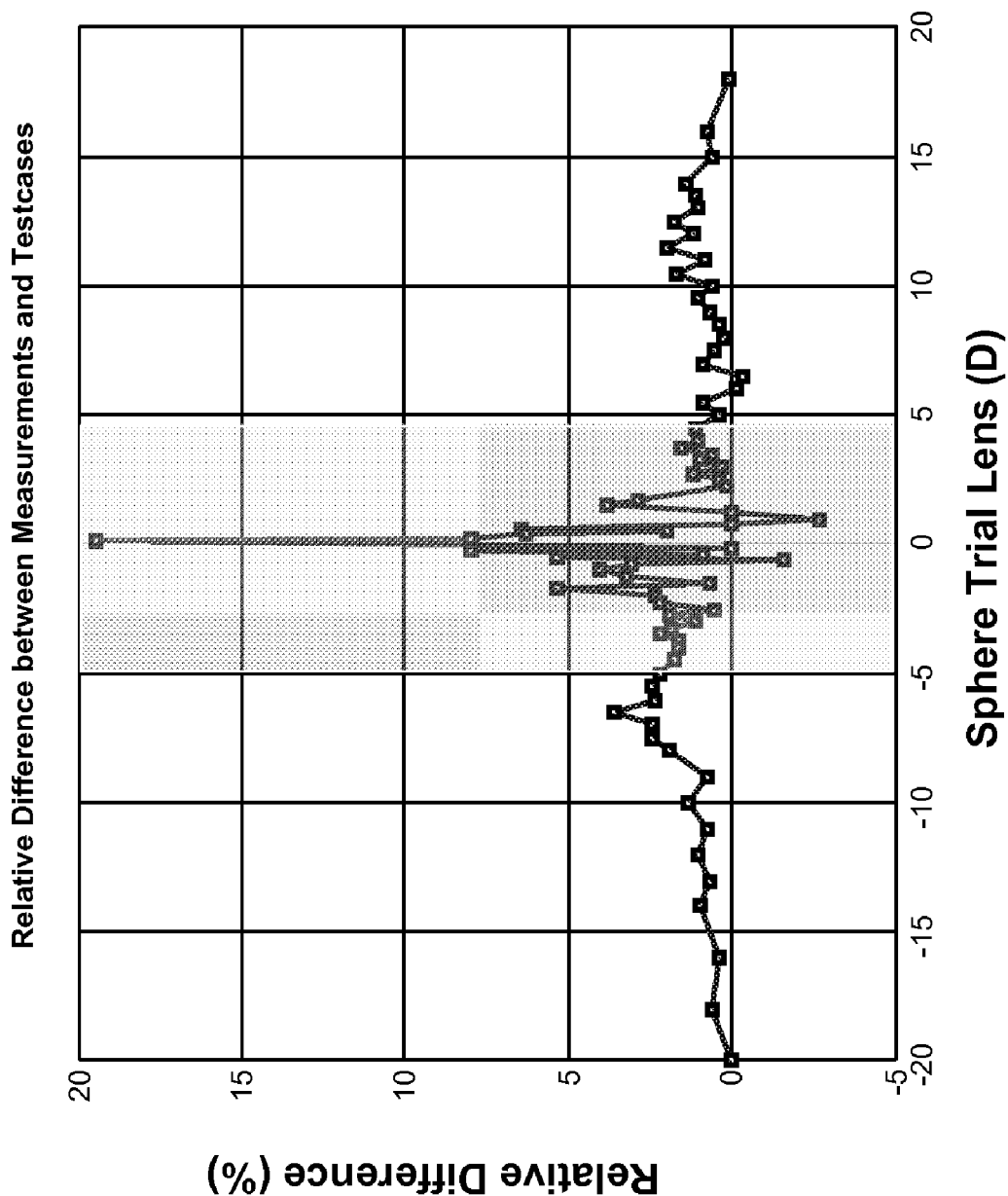
FIG. 26 shows the results of relative difference between measurements and test lenses for spherical test lenses from −20 D to +18 D (Mean relative error: 1.954%, Maximum excluding the gray masked data: 3.58%).
Figure 27:
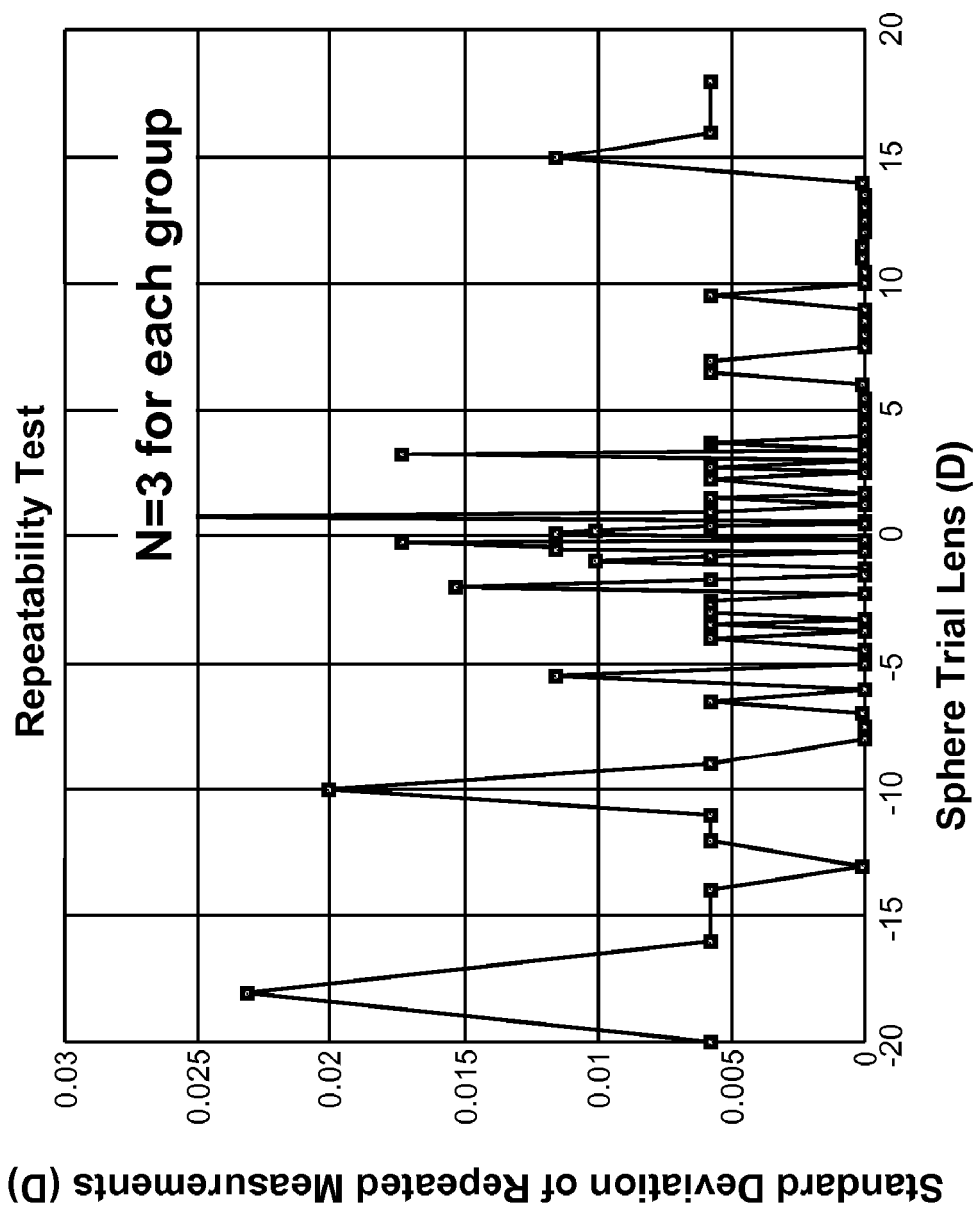
FIG. 27 shows the results of a repeatability test for spherical test lenses from −20 D to +18 D. Maximum deviation was less than 0.03 D.
Figure 28:
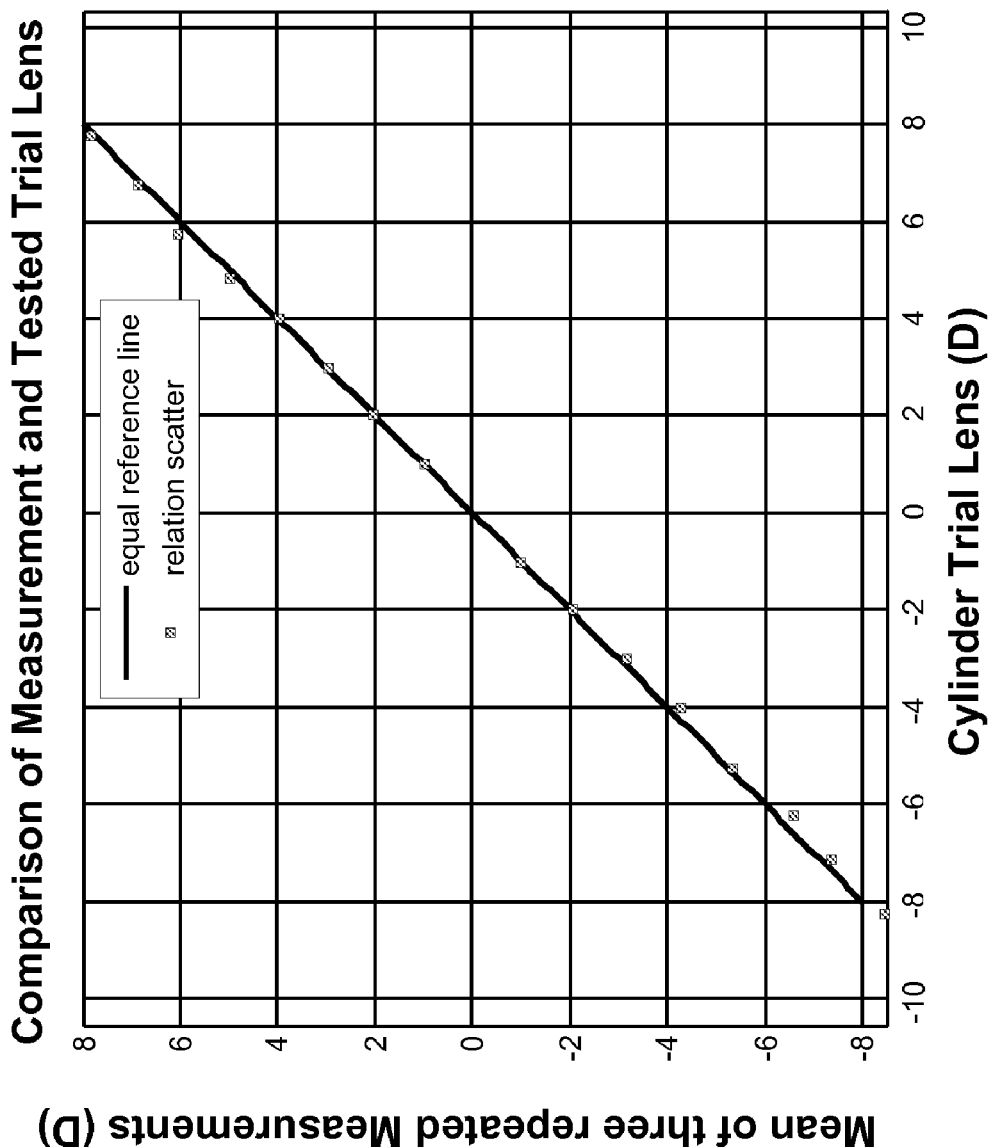
FIG. 28 shows the results of a comparison of measurement and tested trial lenses for cylindrical test lenses from −8 D to +8 D (correlation coefficient r=0.9999).
Figure 29:
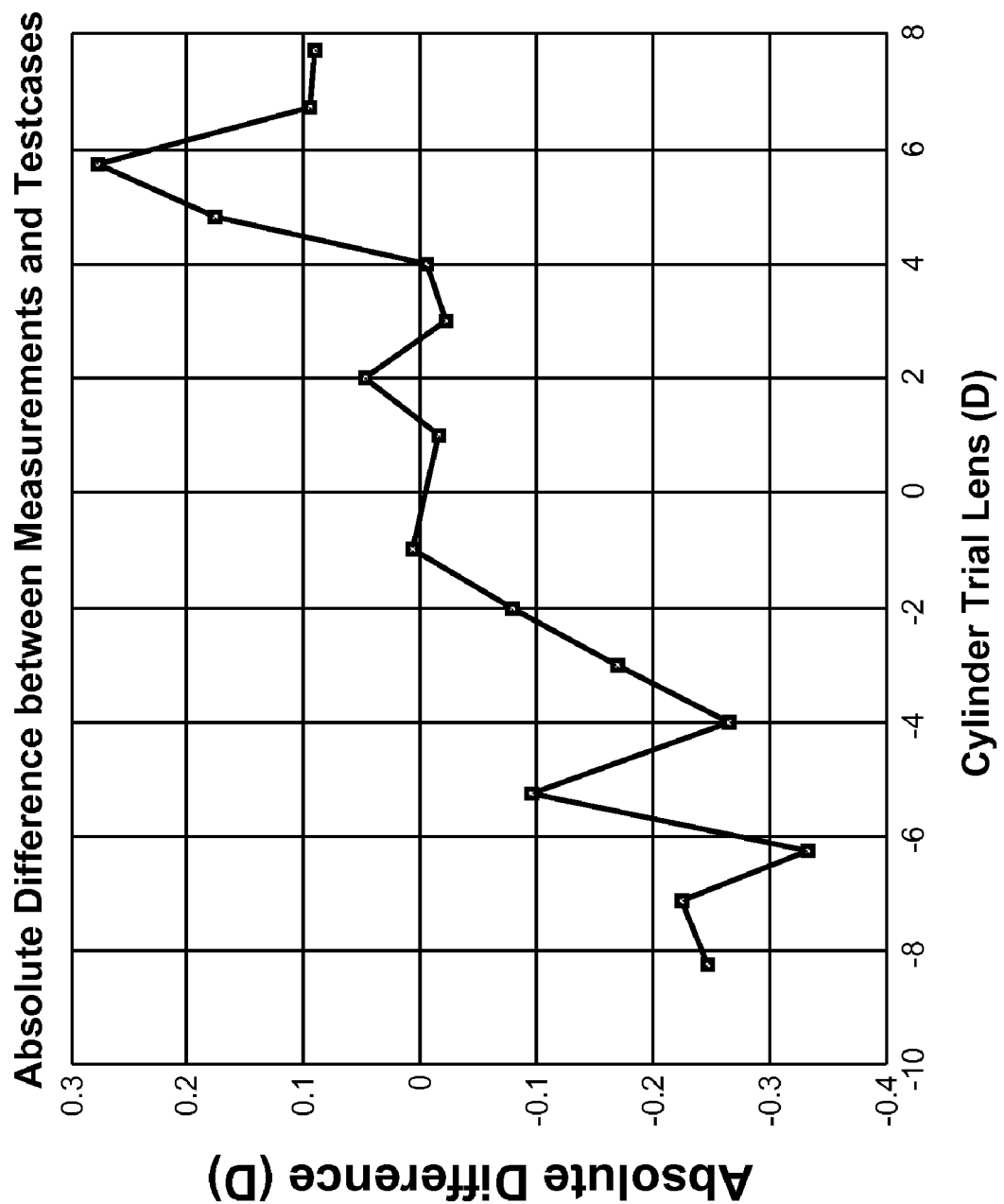
FIG. 29 shows the results of absolute difference between measurements and test lenses for cylindrical test lenses from −8 D to +8 D (Absolute mean difference: 0.1347 D, Maximum difference: 0.33 D).
Figure 30:
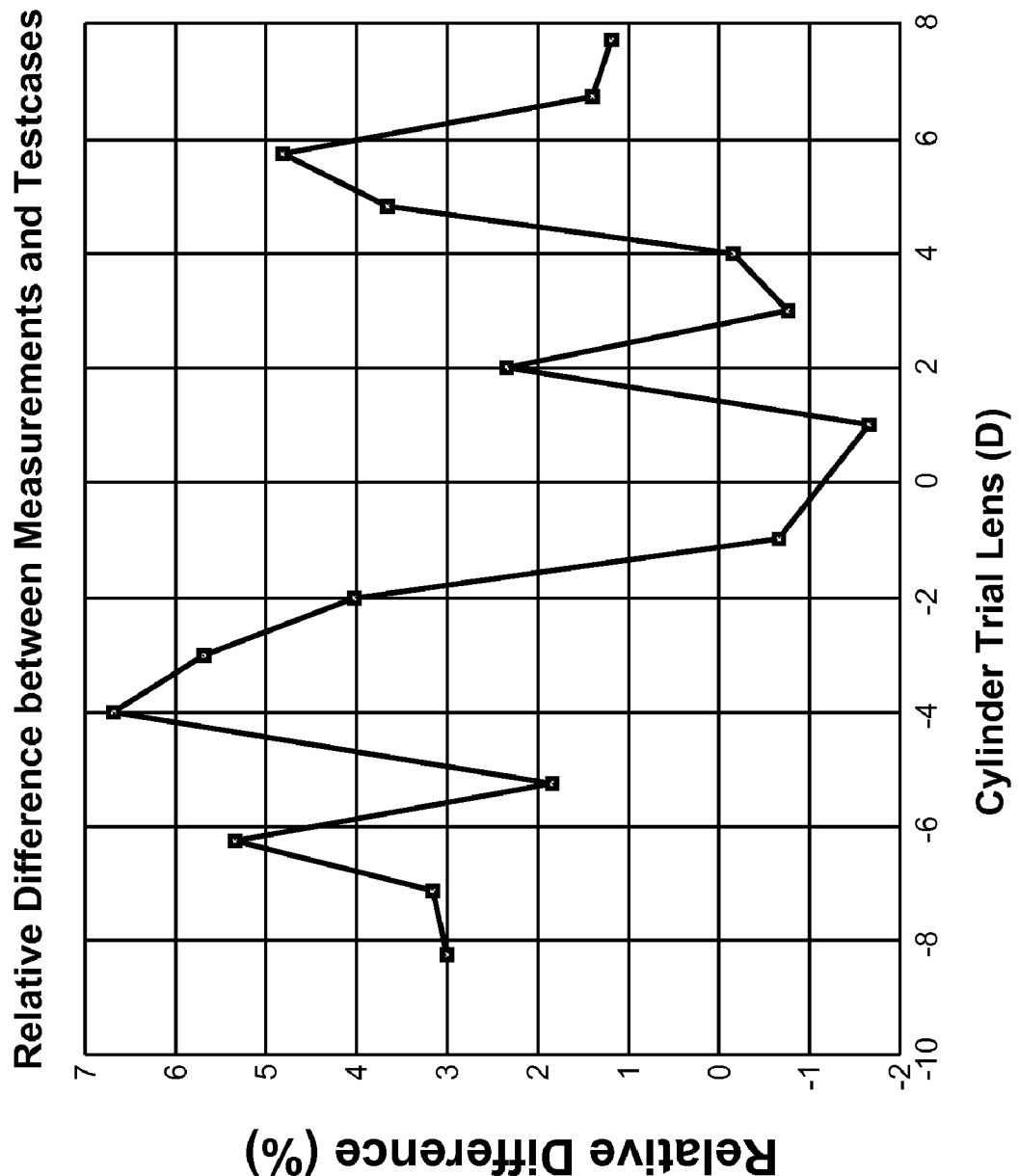
FIG. 30 shows the results of relative difference between measurements and test lenses for cylindrical test lenses from −8 D to +8 D (Mean relative error: 2.8925%).
Figure 31:
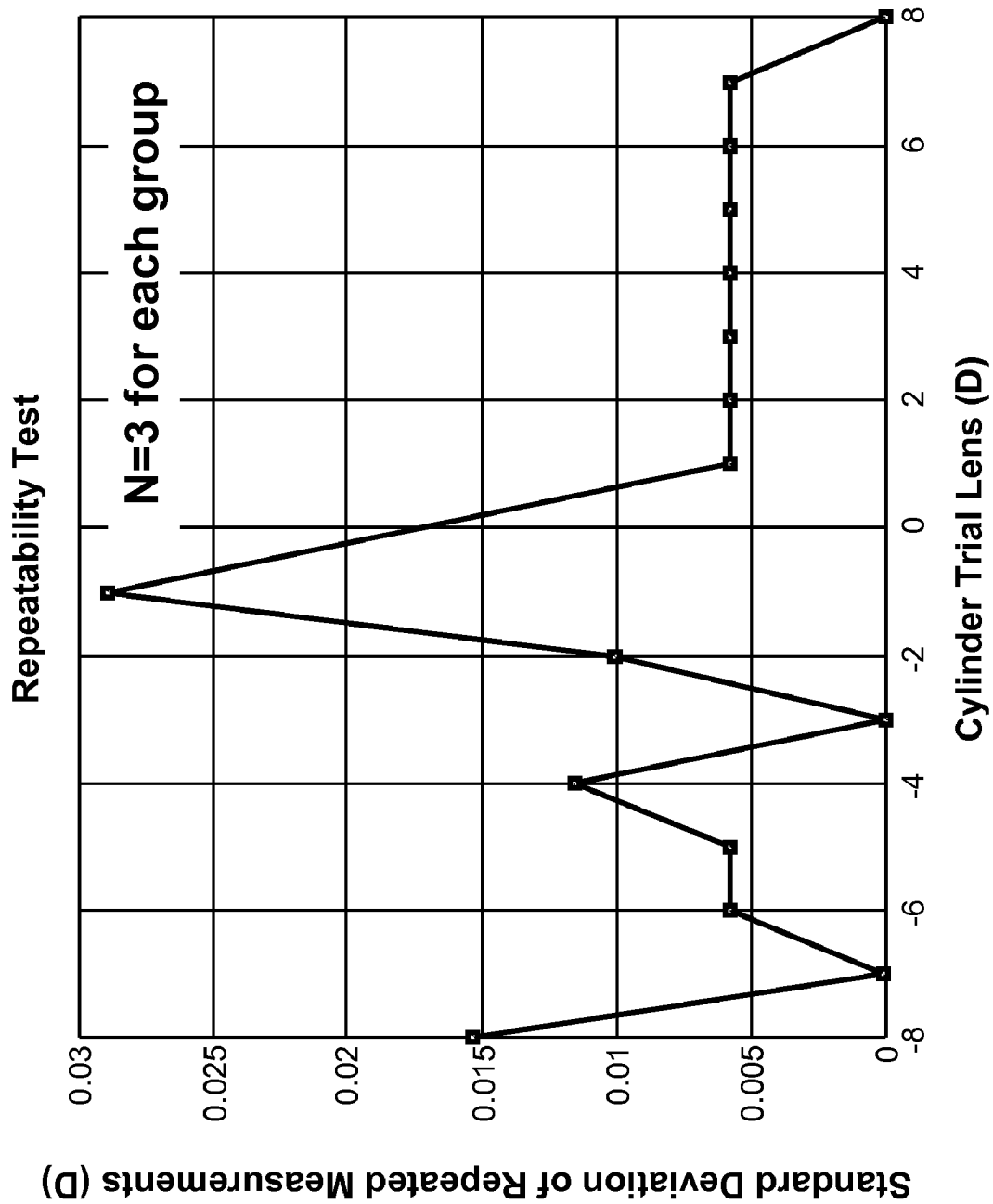
FIG. 31 shows the results of a repeatability test for cylindrical test lenses from −8 D to +8 D. Maximum deviation was less than 0.03 D.

Measurements should be taken to assure tight alignment tolerance (decentration tilt). For example, for accuracy of 0.5 D measured at −20 D, the axial tolerance should be 1.28 mm. As shown in FIG. 23, the amount of measured cylinder was measured using a sphere lens from about −20 D to +18 D with fixed scheme (mean=0.04 D, maximum=0.17 D).

Defocus was accurately measured over a 38 D range and astigmatism over a 16 D range. Correlation coefficients between mean wavefront measurements (n=3) and expected refractions for both sphere and cylinder lenses were 1.00.

For spherical lenses, the instrument was accurate to within 0.2 D over the range from −20 D to +18 D without any means to compensate refraction. Results for spherical test lenses are shown in FIGS. 24-27.

For cylindrical lenses, the instrument was accurate to within 0.15 D over the range from −7 D to +10 D without any means to compensate refraction. The amplitude of measured astigmatism was accurate to within 0.33 D within the range of 16 D (−8 D to +8 D) without any means to compensate refraction. The amplitude of measured astigmatism was accurate to within 0.2 D within the range of 11 D (−3 D to +5 D) without any means to compensate refraction. Results for cylindrical test lenses are shown in FIGS. 28-31.

The repeatability for fixed condition measurements obtained within 2 minutes was within 0.03 D. Improved accuracy would be expected after an optimized calibration that takes component tolerances into account.

These results demonstrate that the Hartmann-Moiré wavefront sensor measures defocus and astigmatism accurately and repeatedly over a large dynamic range of −20 D to +18 D for spherical lenses and over the range of −8 D to 8 D for cylindrical lenses.

EXAMPLE 2

Comparison of Hartmann-Moiré to Talbot-Moiré

Figure 32:
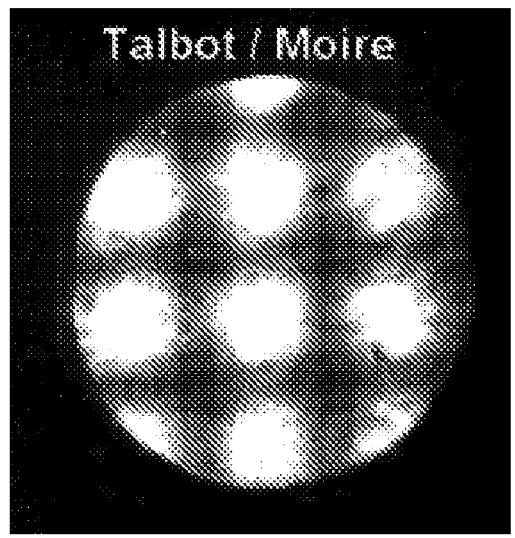
FIG. 32 shows a CCD camera photograph of the shadow patterns created by a comparative Talbot-Moiré wavefront sensor, wherein the two Talbot optics are configured to produce similar sized spot patterns as those depicted in the following Figure.
Figure 33:
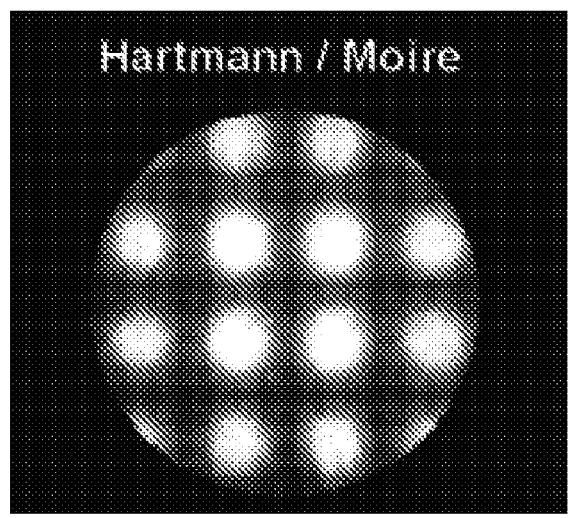
FIG. 33 shows a CCD camera photograph of the spot patterns created by a Hartmann-Moiré wavefront sensor configured to produce similar sized spot patterns as those depicted in the preceding Figure.
Figure 34:
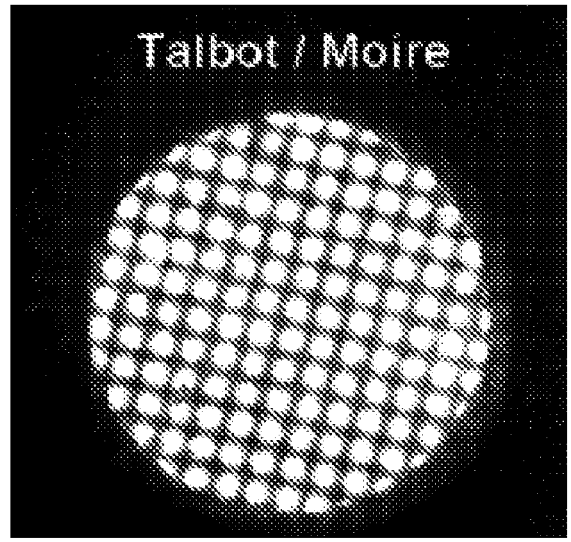
FIG. 34 shows a CCD camera photograph of the shadow patterns created by a comparative Talbot-Moiré wavefront sensor, wherein the two Talbot optics are configured to produce similar sized spot patterns as those depicted in the following Figure.
Figure 35:
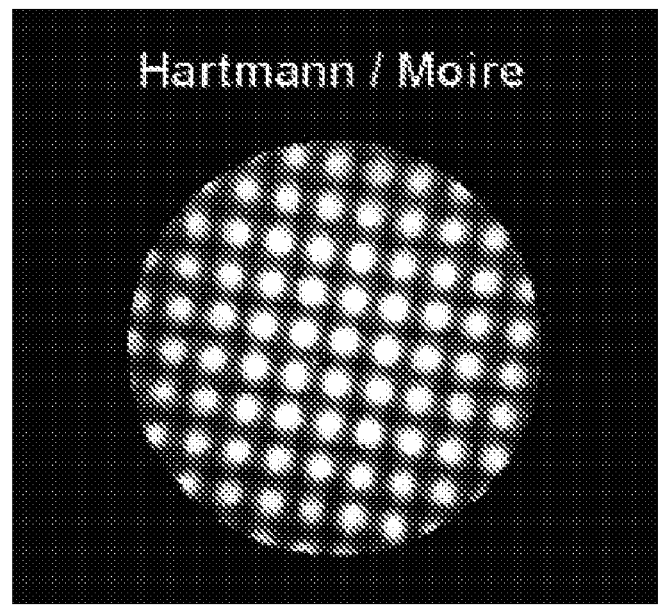
FIG. 35 shows a CCD camera photograph of the spot patterns created by a Hartmann-Moiré wavefront sensor configured to produce similar sized spot patterns as those depicted in the preceding Figure.

FIGS. 32-35 demonstrate the improved image quality achieved by the Hartmann-Moiré wavefront sensor described herein as compared with a Talbot-Moiré wavefront sensor. FIGS. 32 and 34 show CCD camera photographs of the shadow patterns created by a Talbot-Moiré wavefront sensor. FIGS. 33 and 35 show CCD camera photographs of the spot patterns created by a Hartmann-Moiré wavefront sensor configured to produce similar sized spots as the shadows depicted in FIGS. 32 and 34, respectively.

As shown by the comparative figures, the spots formed by the Hartmann-Moiré wavefront sensor are of a high image quality, allowing for a more accurate determination of each spot's center and a more accurate measurement of the spot's movement and position.

EXAMPLE 3

Comparative Examples for Measuring a Model Eye

Figure 36A:
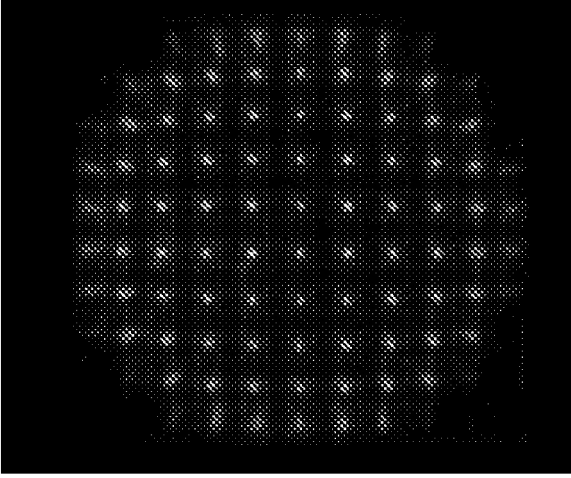
FIGS. 36A and B show images from a comparative Shack-Hartmann device.
Figure 36B:
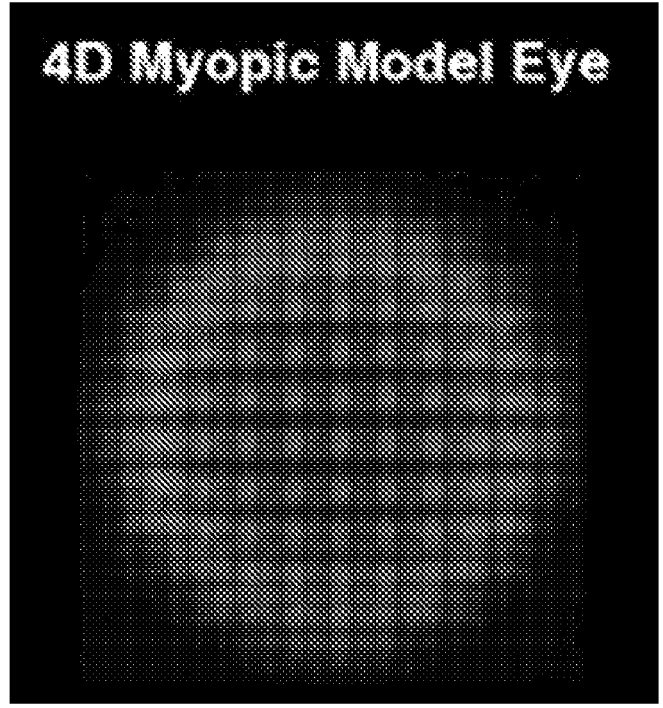
FIG. 36B shows a 4 Diopter eye.

FIG. 36 shows two images from a comparative Shack-Hartmann device. FIG. 36A shows spots of light formed when a plane wave is being measured (i.e., an emmetropic eye), and FIG. 36B shows spots of light formed when the model eye has a converging beam of light emerging from it (i.e., a myopic eye). As the beam of converging light passes through the Shack-Hartmann device, the spots grow closer together, and the amount that they have moved is easily observed. However, at the relatively low optical power of only four Diopters, the spots of light begin to lose their contrast and become blurry. This makes the task of determining the centroid of the spot of light difficult, if not impossible. As the power of the converging light grows beyond four Diopters, the spots of light will get even more blurry, to the point of where the device can no longer make a measurement, which is why this device has a low dynamic range.

Figure 37A:
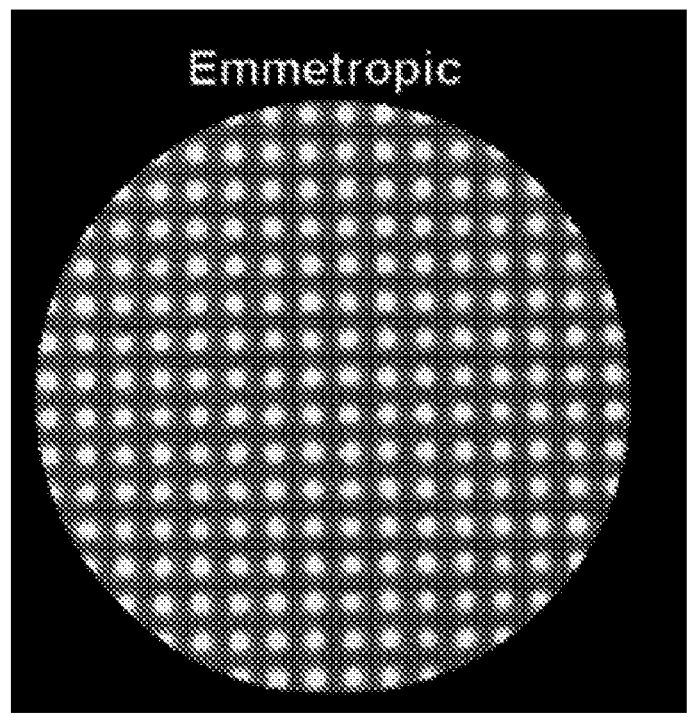
FIGS. 37A and B show two images from a comparative Hartmann Screen device.
Figure 37B:
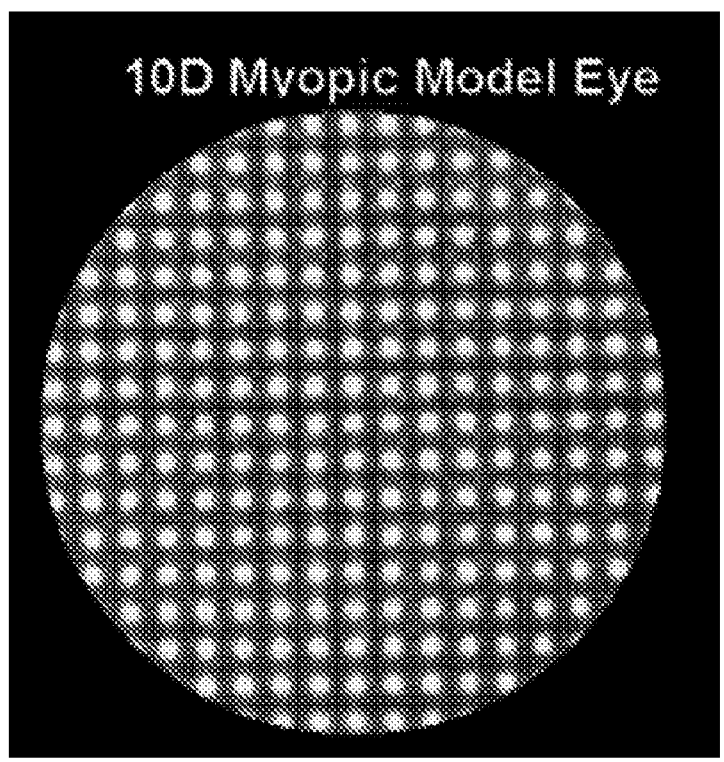
FIG. 37B shows a 10 Diopter eye.

FIG. 37 shows two images from a comparative Hartmann Screen device. FIG. 37A shows spots of light formed when a plane wave is being measured (i.e., an emmetropic eye), and FIG. 37B shows spots of light formed when the model eye has a converging beam of light emerging from it (i.e., a myopic eye). As the beam of converging light passes through the Hartmann device, the spots grow closer together, but the amount that they have moved is very small. Although at the relatively high optical power of ten Diopters the spots continue to have high contrast and are in sharp focus, the amount of movement of the spots is much smaller than the amount of movement of the spots in the Shack-Hartmann device, which is why this device has low sensitivity.

Figure 38A:
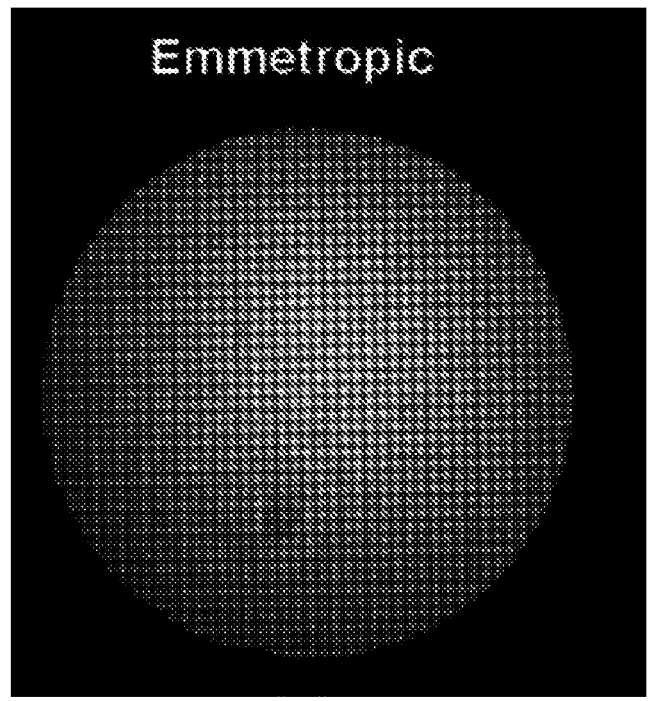
FIGS. 38A and B show two images from a Hartmann-Moiré device.
Figure 38B:
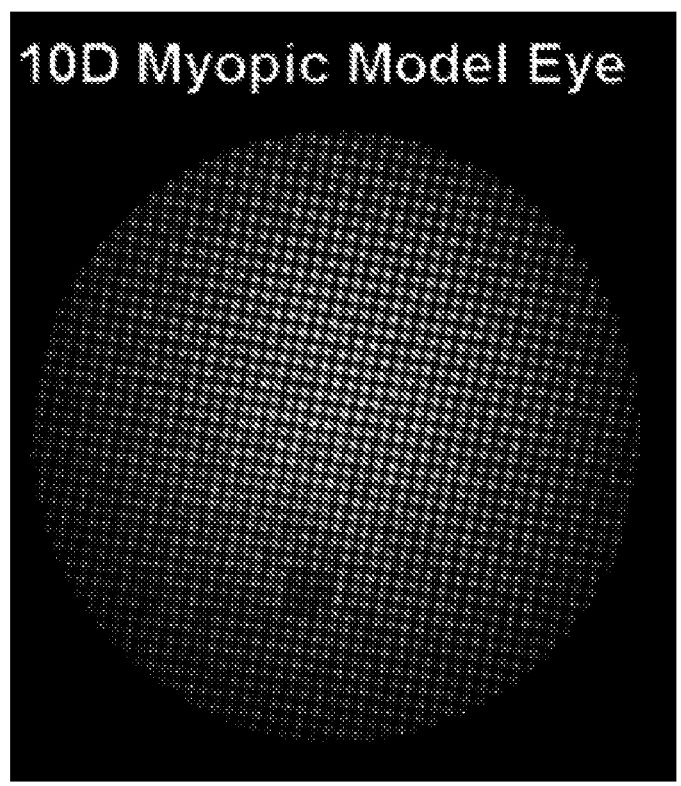
FIG. 38B shows a 10 Diopter eye.

FIG. 38 shows two images from a Hartmann-Moiré device as described herein. FIG. 38A shows spots of light formed when a plane wave is being measured (i.e., an emmetropic eye), and FIG. 38B shows spots of light formed when the model eye has a converging beam of light emerging from it (i.e., a myopic eye). As the beam of converging light passes through the Hartmann-Moiré device, the spots rotate clockwise, and the amount that they have moved is easily observed. Even at the relatively high optical power of ten Diopters the spots continue to have high contrast and are in sharp focus, which is why this device has both high sensitivity and a high dynamic range.

What is claimed is:

1. An apparatus comprising:
   a) a first screen comprising a first two-dimensional array of spaced circular apertures, wherein the first screen is placed downstream of a light source;
   b) a second screen comprising a second two-dimensional array of spaced circular apertures, wherein the second screen is placed downstream of the first screen, the second screen is in a plane parallel to the first screen, and the second screen is rotated relative to the first screen; and
   c) a light detector downstream of the second screen.

2. The apparatus of claim 1, wherein the first two-dimensional array and the second two-dimensional array are identical.

3. The apparatus of claim 1, wherein at least one screen is a Hartmann screen.

4. The apparatus of claim 3, wherein the first screen and the second screen are Hartmann screens.

5. The apparatus of claim 1, wherein at least one spaced circular aperture of the first screen or second screen includes a lenslet.

6. The apparatus of claim 5, wherein each of the spaced Circular apertures of the first screen and the second screen includes a lenslet.

7. The apparatus of claim 1, wherein the second screen is rotated about 1 to about 30 degrees relative to the first screen.

8. The apparatus of claim 1, further comprising a lens.

9. The apparatus of claim 8, wherein the lens is placed between the second screen and the light detector.

10. The apparatus of claim 8, wherein the lens is placed upstream of the first screen.

11. The apparatus of claim 1, further comprising a beam splitter positioned upstream of the first screen.

12. The apparatus of claim 1, wherein at least one of the first and second screens is substantially opaque in the area surrounding the circular apertures.

13. The apparatus of claim 1, wherein the circular apertures of at least one of the first screen and the second screen are spaced apart by about 0.0002 inch to about 0.02 inch.

14. A method of measuring characteristics of a lens comprising:
   a) directing light from a light source into the lens;
   b) directing the light from the lens through a first screen comprising a first two-dimensional array of spaced circular apertures;
   c) directing the light from the first screen through a second screen comprising a second two-dimensional array of spaced circular apertures, wherein the second screen is placed downstream of the first screen, the second screen is in a plane parallel to the first screen, and the second screen is rotated relative to the first screen;

d) detecting the light from the second screen at a light detector.

15. The method of claim 14, wherein the first two-dimensional array and the second two-dimensional array are identical.

16. The method of claim 14, wherein at least one screen is a Hartmann screen.

17. The method of claim 16, wherein the first screen and the second screen are Hartmann screens.

18. The method of claim 14, wherein at least one spaced circular aperture of the first screen or second screen includes a lenslet.

19. The method of claim 18, wherein each of the spaced circular apertures of the first screen and the second screen includes a lenslet.

20. The method of claim 14, wherein the second screen is rotated about 1 to about 30 degrees relative to the first screen.

21. The method of claim 14, further comprising directing the light through a relay lens.

22. The method of claim 21, wherein the relay lens is placed between the second screen and the light detector.

23. The method of claim 21, wherein the relay lens is placed upstream of the first screen.

24. The method of claim 14, further comprising directing the light to a beam splitter positioned upstream of the first screen.

25. The method of claim 14, further comprising selecting a distance between the light source and the first screen, and maintaining the light source stationary during measurement.

26. A method of measuring characteristics of an eye comprising:

a) directing light into the eye;

b) directing the light from the eye through a first screen comprising a first two-dimensional array of spaced circular apertures;

c) directing the light from the first screen through a second screen comprising a second two-dimensional array of spaced circular apertures, wherein the second screen is placed downstream of the first screen, the second screen is in a plane parallel to the first screen, and the second screen is rotated relative to the first screen;

d) detecting the light from the second screen at a light detector.

27. The method of claim 26, wherein the first two-dimensional array and the second two-dimensional array are identical.

28. The method of claim 26, wherein at least one screen is a Hartmann screen.

29. The method of claim 28, wherein the first screen and the second screen are Hartmann screens.

30. The method of claim 26, wherein at least one spaced circular aperture of the first screen or second screen includes a lenslet.

31. The method of claim 30, wherein each of the spaced circular apertures of the first screen and the second screen includes a lenslet.

32. The method of claim 26, wherein the second screen is rotated about 1 to about 30 degrees relative to the first screen.

33. The method of claim 26, further comprising directing the light through a relay lens.

34. The method of claim 33, wherein the relay lens is placed between the second screen and the light detector.

35. The method of claim 33, wherein the relay lens is placed upstream of the first screen.

36. The method of claim 26, further comprising directing the light to a beam splitter positioned upstream of the first screen.

\* \* \* \* \*